(12) United States Patent
Morishita

(10) Patent No.: US 11,114,097 B2
(45) Date of Patent: Sep. 7, 2021

(54) NOTIFICATION SYSTEM, NOTIFICATION METHOD, AND NON-TRANSITORY COMPUTER READABLE MEDIUM STORING PROGRAM

(71) Applicant: NEC CORPORATION, Tokyo (JP)

(72) Inventor: Shota Morishita, Tokyo (JP)

(73) Assignee: NEC CORPORATION, Tokyo (JP)

( * ) Notice: Subject to any disclaimer, the term of this patent is extended or adjusted under 35 U.S.C. 154(b) by 0 days.

(21) Appl. No.: 16/615,484

(22) PCT Filed: Jun. 12, 2018

(86) PCT No.: PCT/JP2018/022432
§ 371 (c)(1),
(2) Date: Nov. 21, 2019

(87) PCT Pub. No.: WO2018/230562
PCT Pub. Date: Dec. 20, 2018

(65) Prior Publication Data
US 2020/0211547 A1 Jul. 2, 2020

(30) Foreign Application Priority Data
Jun. 14, 2017 (JP) .............................. JP2017-117008

(51) Int. Cl.
*G06F 16/61* (2019.01)
*G10L 15/22* (2006.01)
(Continued)

(52) U.S. Cl.
CPC .............. *G10L 15/22* (2013.01); *G06F 16/61* (2019.01); *G06F 16/683* (2019.01); *G08B 21/02* (2013.01);
(Continued)

(58) Field of Classification Search
None
See application file for complete search history.

(56) References Cited

U.S. PATENT DOCUMENTS 9,070,357 B1* 6/2015 Kennedy ................ G06Q 50/22
2010/0127878 A1* 5/2010 Wang ...................... G10L 17/26
340/573.1

(Continued)

FOREIGN PATENT DOCUMENTS

| JP | 2005-032139 A | 2/2005 |
| JP | 2007-004662 A | 1/2007 |
| JP | 2016-148991 A | 8/2016 |

OTHER PUBLICATIONS

International Search Report for PCT/JP2018/022432 dated Jul. 17, 2018 [PCT/ISA/210].
(Continued)

*Primary Examiner* — Brent Swarthout
(74) *Attorney, Agent, or Firm* — Sughrue Mion, PLLC

(57) ABSTRACT

Included are calling means (110) for making a call to a communication terminal (200) possessed by a target person, a database (120) configured to store in advance speech data of the target person, comparison means (130) for comparing a tone of speech data transmitted from the communication terminal with a tone of the speech data stored in the database (120), and notification means (140) for issuing a predetermined notification when a difference between the tone of the speech data transmitted from the communication terminal (200) and the tone of the speech data stored in the database (120) is determined to be outside a predetermined range as a result of the comparison by the comparison means (130). With this configuration, it is possible to obtain correct information about a condition of the target person.

11 Claims, 27 Drawing Sheets

(51) Int. Cl.
- *G06F 16/683* (2019.01)
- *G08B 21/02* (2006.01)
- *G10L 15/30* (2013.01)
- *G10L 25/51* (2013.01)
- *G10L 25/90* (2013.01)
- *H04M 11/08* (2006.01)

(52) U.S. Cl.
CPC .............. *G10L 15/30* (2013.01); *G10L 25/51* (2013.01); *G10L 25/90* (2013.01); *H04M 11/08* (2013.01)

(56) References Cited

U.S. PATENT DOCUMENTS

| | | | | |
|---|---|---|---|---|
| 2016/0026773 | A1* | 1/2016 | Chu .......................... | A61J 7/02 |
| | | | | 705/2 |
| 2018/0296092 | A1* | 10/2018 | Hassan ................ | A61B 5/0022 |
| 2018/0322961 | A1* | 11/2018 | Kim ....................... | G16H 10/20 |

OTHER PUBLICATIONS

Written Opinion for PCT/JP2018/022432 dated Jul. 17, 2018 [PCT/ISA/237].

* cited by examiner

| TELEPHONE NUMBER | E-MAIL ADDRESS | SPEECH DATA (TONE) |
|---|---|---|
| ... | ... | ○···<br>○···<br>○···<br>○···<br>○··· |
| ⋮ | ⋮ | ⋮ |

Fig. 5

| TELEPHONE NUMBER | E-MAIL ADDRESS | QUESTION | ANSWER |
|---|---|---|---|
| ... | ... | ... | ... |
| | | ... | ... |
| | | ... | ... |
| | | ... | ... |
| ⋮ | ⋮ | ⋮ | ⋮ |

Fig. 14

| TELEPHONE NUMBER | E-MAIL ADDRESS | OPERATION ITEM | OPERATION RANGE |
|---|---|---|---|
| ... | ... | TIME TO ANSWER CALL | XX-XX SECONDS |
| | | TIME TO HANG UP CALL | XX-XX MINUTES |
| | | TIME FROM QUESTION TO ANSWER | XX-XX SECONDS |
| | | ... | ... |
| ⋮ | ⋮ | ⋮ | ⋮ |

Fig. 23

NOTIFICATION SYSTEM, NOTIFICATION METHOD, AND NON-TRANSITORY COMPUTER READABLE MEDIUM STORING PROGRAM

CROSS REFERENCE TO RELATED APPLICATIONS

This application is a National Stage of International Application No. PCT/JP2018/022432 filed Jun. 12, 2018, claiming priority based on Japanese Patent Application No. 2017-117008 filed Jun. 14, 2017, the entire disclosure of which is incorporated herein.

TECHNICAL FIELD

The present disclosure relates to a notification system, a notification method, and a program.

BACKGROUND ART

Recently in this aging society, there are more elderly living alone.

Various services have been proposed for watching such elderly living alone. For example, there is a system being studied in which a person is detected using a sensor attached to a refrigerator, speech control is performed on the person (target person), voice data input by the target person in response to the speech control is analyzed to acquire his/her state of safety, and a result of the acquisition is presented (e.g., see Patent Literature 1).

CITATION LIST

Patent Literature

Patent Literature 1: Japanese Unexamined Patent Application Publication No. 2016-148991

SUMMARY OF INVENTION

Technical Problem

The above-described technology performs text analysis on input voice data and determines the state of safety based on a content of the analyzed text. Therefore, even when the target person is feeling ill, if the same wording (text) as that when he/she is feeling well is input, the system determines that the condition of the target person is good. The above-described technology thus has a problem that correct information about the condition of the target person may not be obtained.

An object of the present disclosure is to provide a notification system, a notification method, and a program that solve the above-described problem.

Solution to Problem

A notification system according to the present disclosure includes:

calling means for making a call to a communication terminal possessed by a target person;

a database configured to store in advance speech data of the target person;

comparison means for comparing a tone of speech data transmitted from the communication terminal with a tone of the speech data stored in the database; and notification means for issuing a predetermined notification when a difference between the tone of the speech data transmitted from the communication terminal and the tone of the speech data stored in the database is determined to be outside a predetermined range as a result of the comparison by the comparison means.

A notification method according to the present disclosure includes:

a process of making a call to a communication terminal possessed by a target person;

a process of comparing a tone of speech data transmitted from the communication terminal with a tone of the speech data stored in a database which stores speech data of the target person in advance; and a process of issuing a predetermined notification when a difference between the tone of the speech data transmitted from the communication terminal and the tone of the speech data stored in the database is determined to be outside a predetermined range as a result of the comparison.

A program according to the present disclosure causes a computer to execute:

a procedure of making a call to a communication terminal possessed by a target person;

a procedure of comparing a tone of speech data transmitted from the communication terminal with a tone of the speech data stored in a database which stores speech data of the target person in advance; and a procedure of issuing a predetermined notification when a difference between the tone of the speech data transmitted from the communication terminal and the tone of the speech data stored in the database is determined to be outside a predetermined range as a result of the comparison.

Advantageous Effects of Invention

As described above, according to the present disclosure, it is possible to obtain correct information about a condition of a target person.

BRIEF DESCRIPTION OF DRAWINGS

FIG. 5 is a diagram showing an example of speech data stored in a database shown in FIG. 4;

FIG. 14 is a diagram showing an example of associations between questions and answers stored in a database shown in FIG. 13;

FIG. 23 is a diagram showing an example of an operation method of a communication terminal stored in a database shown in FIG. 22;

DESCRIPTION OF EMBODIMENTS

Embodiments of the present disclosure will be described below with reference to the drawings.

First Embodiment

Figure 1:
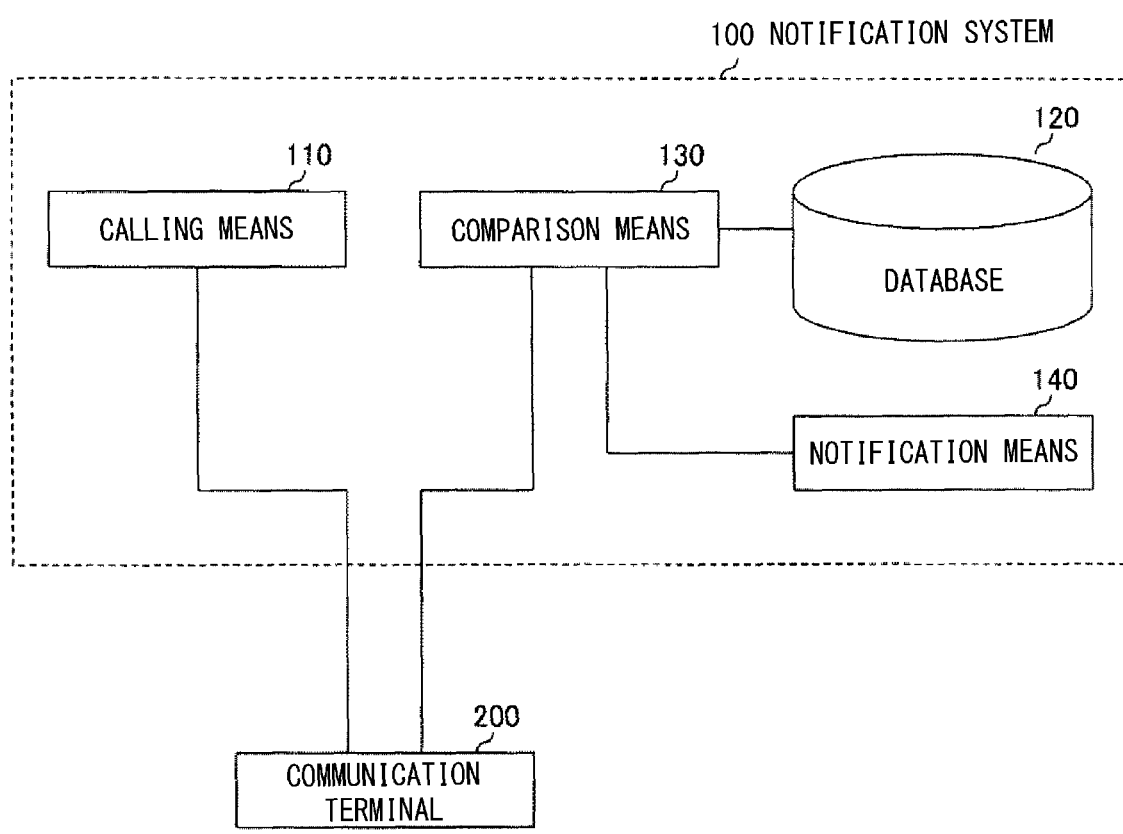
FIG. 1 is a diagram showing a first embodiment of a notification system according to the present disclosure.

FIG. 1 is a diagram showing a first embodiment of a notification system according to the present disclosure. As shown in FIG. 1, a notification system 100 according to this embodiment includes calling means 110, a database 120, comparison means 130, and notification means 140.

The calling means 110 makes a call to a communication terminal 200 possessed by a target person.

The database 120 stores the target person's speech data in advance.

The comparison means 130 compares a tone of speech data transmitted from the communication terminal 200 with a tone of the speech data stored in the database 120.

When a difference between the tone of the speech data transmitted from the communication terminal 200 and the tone of the speech data stored in the database 120 is determined to be outside a predetermined range as a result of the comparison by the comparison means 130, the notification means 140 makes a predetermined notification.

Figure 2:
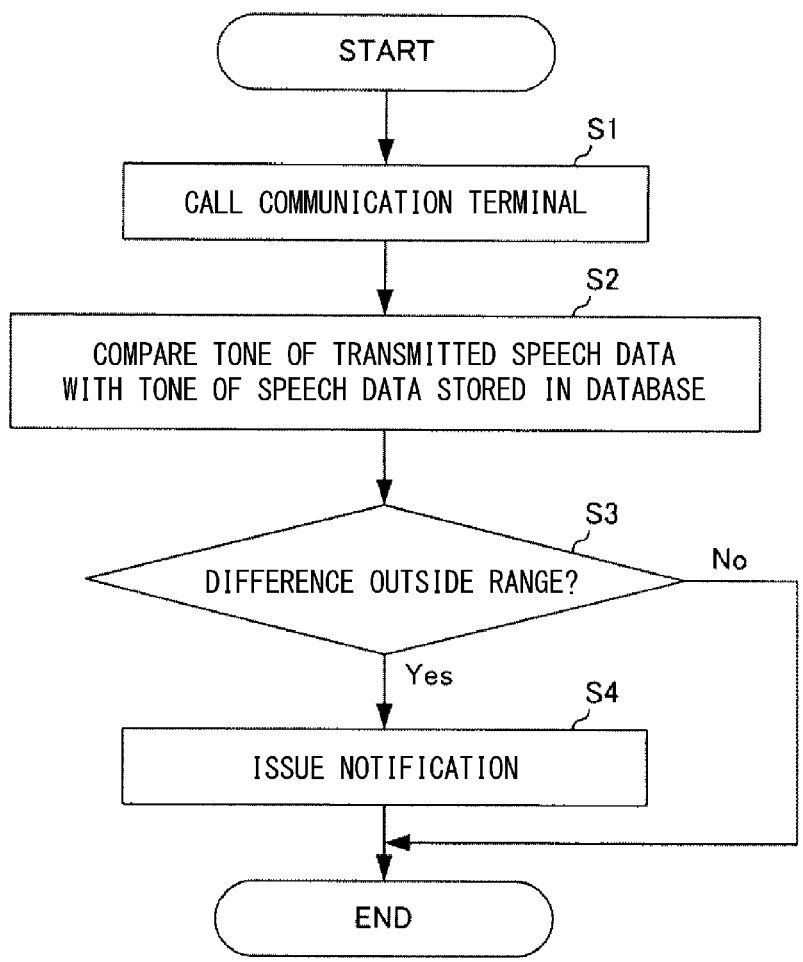
FIG. 2 is a flowchart for describing an example of a notification method in the notification system shown in FIG. 1.

A notification method in the notification system 100 shown in FIG. 1 will be described below. FIG. 2 is a flowchart for describing an example of the notification method in the notification system 100 shown in FIG. 1.

First, the calling means 110 makes a call to the communication terminal 200 possessed by the target person (Step S1). After that, when speech data is transmitted from the communication terminal 200, the comparison means 130 compares a tone of the speech data transmitted from the communication terminal 200 with a tone of the speech data stored in the database 120 (Step S2). As a result of the comparison, the comparison means 130 determines whether the difference between the tone of the speech data transmitted from the communication terminal 200 and the tone of the speech data stored in the database 120 is outside a predetermined range (Step S3). When the difference between the tone of the speech data transmitted from the communication terminal 200 and the tone of the speech data stored in the database 120 is determined to be outside the predetermined range as a result of the comparison by the comparison means 130, the notification means 140 issues a predetermined notification (Step S4).

As described above, when the difference between the tone of the speech data transmitted from the communication terminal 200 and the tone of the speech data registered in advance is determined to be outside the predetermined range, the notification system 100 according to this embodiment issues a notification. Thus, it is possible to obtain correct information about the condition of the target person who possesses the communication terminal 200.

Second Embodiment

Figure 3:
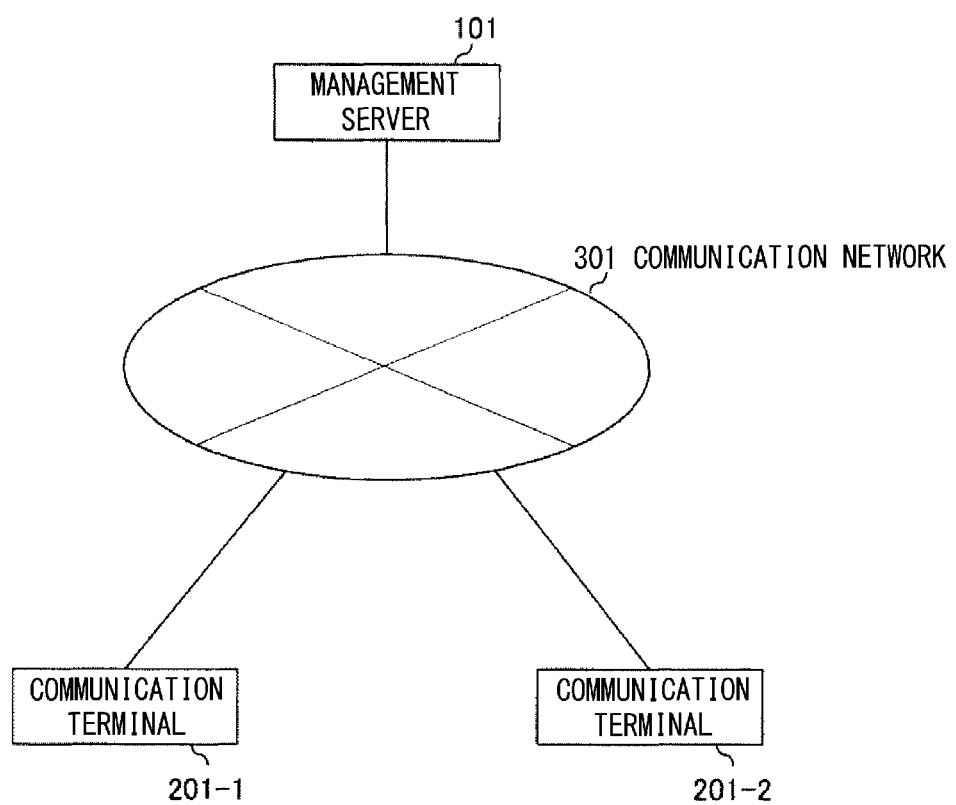
FIG. 3 is a diagram showing a second embodiment of a notification system according to the present disclosure.

FIG. 3 is a diagram showing a second embodiment of the notification system according to the present disclosure. The notification system according to this embodiment is implemented by an apparatus of a management server 101. As shown in FIG. 3, this embodiment includes the management server 101 that is a notification system and communication terminals 201-1 and 201-2. The management server 101 is connected the communication terminals 201-1 and 201-2 via a communication network 301.

The communication terminal 201-1 is a communication apparatus such as a mobile terminal possessed by the target person. The communication terminal 201-2 is a communication apparatus such as a mobile terminal possessed by the target person's family or relatives. Telephone numbers and e-mail addresses of the communication terminals 201-1 and 201-2 are registered in advance in the management server 101 in association with the respective communication terminals 201-1 and 201-2.

Figure 4:
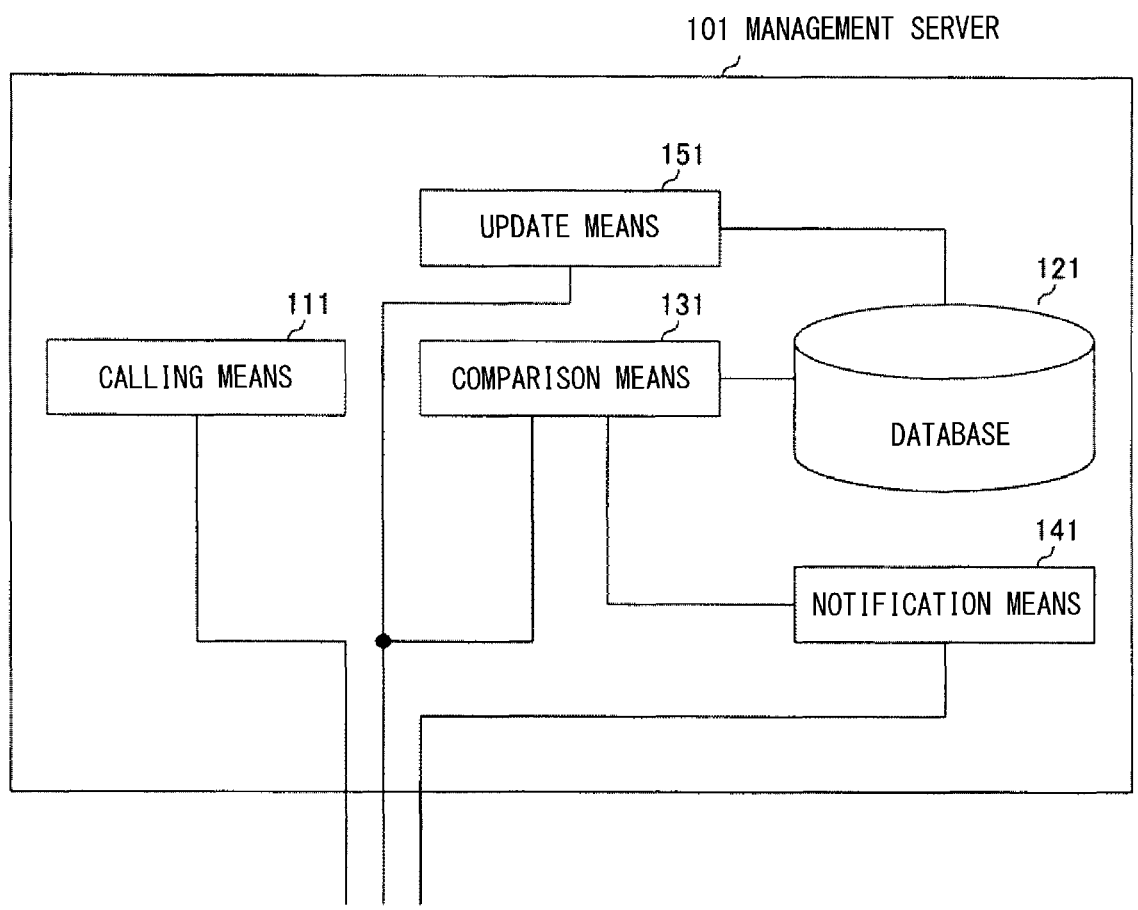
FIG. 4 is a diagram showing an example of an internal configuration of a management server shown in FIG. 3.

FIG. 4 is a diagram showing an example of an internal configuration of the management server 101 shown in FIG. 3. As shown in FIG. 4, the management server 101 shown in FIG. 3 includes calling means 111, a database 121, comparison means 131, notification means 141, and update means 151. FIG. 4 shows an example of main components regarding this embodiment among the components included in the management server 101 shown in FIG. 3.

The calling means 111 makes a call to the communication terminal 201-1 possessed by the target person. When the communication terminal 201-1 responds to the call after the calling means 111 makes the call to the communication terminal 201-1, the calling means 111 transmits to the communication terminal 201-1 a message or guidance for prompting the target person to speak. This message or guidance may be registered in the database 121 in advance. This message or guidance may be, for example, a greeting such as "Good morning" or a question such as a quiz, and prompts the target person to speak. When the message or guidance is a question, this question preferably suits the target person's preference and may be stored in the database 121 in association with the target person in advance. Alternatively, the calling means 111 may use artificial intelligence technology to analyze the target person's preference based on a content spoken by the target person and a content stored in the database 121 and to question according to the analyzed preference. By using the question associated with the target person, it is possible to prompt the target person to answer the question without making him/her bored.

The database 121 stores the speech data of the target person in advance. Specifically, the database 121 stores in advance data indicating a tone when the target person speaks. Here, the stored tone is a tone analyzed (extracted) from the speech data when the target person speaks in a usual state. This tone may be, for example, any combination of a pitch (sound), speaking speed, intonation, accent, etc. of the target person's speaking voice or any one of them. The database 121 further stores in advance the telephone number and the e-mail address of the communication terminal 201-1 in association with the telephone number and the e-mail address of the communication terminal 201-2.

FIG. 5 is a diagram showing an example of the speech data stored in the database 121 shown in FIG. 4. As shown in FIG. 5, the database 121 shown in FIG. 4 stores the telephone number, e-mail address, and speech data (tone) of the target person in association with each other. Here, a plurality of speech data (tone) pieces are associated with one telephone number and one e-mail address. This is to make it possible to more accurately determine the condition of the target person using a plurality of wordings for one target person.

The comparison means 131 compares the tone of the speech data transmitted from the communication terminal 201-1 with the tone of the speech data stored in the database 121. The comparison means 131 determines whether the difference between the tone of the speech data transmitted from the communication terminal 201-1 and the tone of the speech data stored in the database 121 is outside a predetermined range as a result of the comparison. For example, regarding the pitch (tone) of the target person's voice as a tone, the comparison means 131 determines whether a difference between the voice pitch of the speech data transmitted from the communication terminal 201-1 and the voice pitch of the speech data stored in the database 121 is outside a predetermined range. The predetermined range is set in advance and may be registered in the database 121. For example, by the comparison means 131 comparing the above voice pitches, it is possible to detect that the target person is speaking at a pitch much lower than a usual pitch (one stored in the database 121) due to him/her feeling ill. Consequently, it is possible to recognize that the target person is feeling ill. Similarly, for the speaking speed, intonation, accent, etc., the comparison means 131 compares the one transmitted from the communication terminal 201-1 with the usual one registered in the database 121 in advance, and determines a difference between them, so that it is possible to recognize that the target person is feeling ill.

When the difference determined by the comparison means 131 is outside the predetermined range as a result of the comparison by the comparison means 131, the notification means 141 issues a predetermined notification. The notification means 141 issues this notification to the communication terminal 201-1. Alternatively, the notification means 141 issues this notification to the communication terminal 201-2. Further alternatively, the notification means 141 issues this notification to both the communication terminal 201-1 and the communication terminal 201-2. The notification means 141 may issue the notification using an e-mail, an SMS (Short Message Service), a voice call, or other transmission media. Note that the notification means 141 may issue a notification when the state in which the difference between the pitch, speaking speed, intonation, accent, etc. of the speech data transmitted from the communication terminal 201-1 and those of the speech data stored in the database 121 determined by the comparison means 131 is outside the predetermined range continues for a predetermined period such as a few days. A content of this notification indicates, for example, that the condition of the target person seems to be different from usual or suggests an action to be taken.

The update means 151 updates the speech data stored in the database 121 based on the speech data in the call with the communication terminal 201-1. That is, the update means 151 learns the speech data in the call with the communication terminal 201-1 and reflects the learned result in the database 121.

Figure 6:
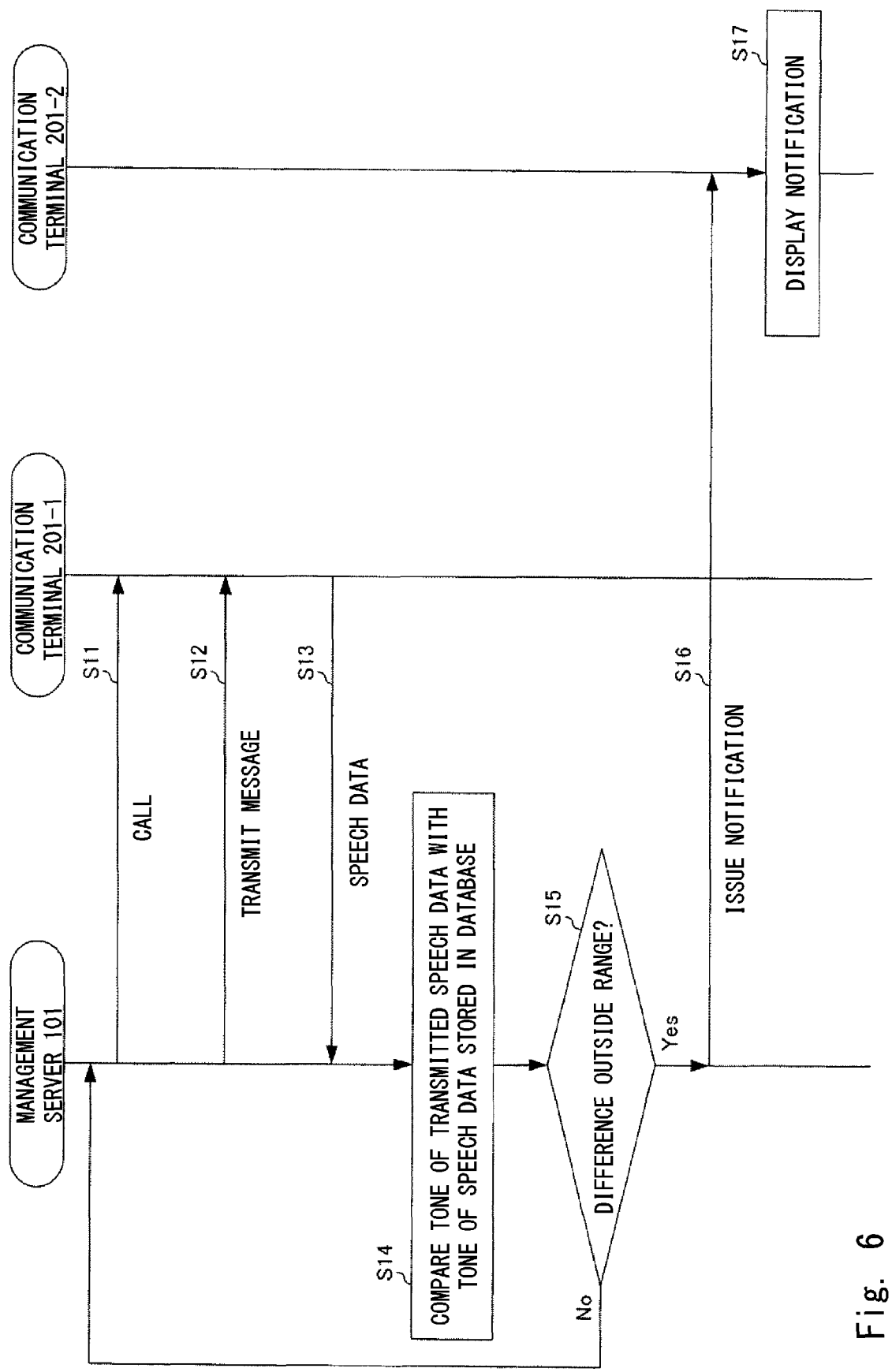
FIG. 6 is a sequence diagram for describing an example of a notification method in the notification system shown in FIG. 3.

The notification method in the notification system shown in FIG. 3 will be described below. FIG. 6 is a sequence diagram for describing an example of the notification method in the notification system shown in FIG. 3. Here, a case where a notification destination to which the notification means 141 shown in FIG. 4 issues a notification is the communication terminal 201-2 will be described as an example.

First, the calling means 111 makes a call to the communication terminal 201-1 possessed by the target person (Step S11). When the communication terminal 201-1 responds (is hooked off), the calling means 111 transmits a message (or guidance) to the communication terminal 201-1 (Step S12).

After that, when an owner of the communication terminal 201-1 speaks, the communication terminal 201-1 transmits the speech data to the management server 101 (Step S13).

When the speech data is transmitted from the communication terminal 201-1, the comparison means 131 compares the tone of the speech data transmitted from the communication terminal 201-1 with the tone of the speech data stored in the database 121 (Step S14). Specifically, the comparison means 131 reads the tone of the speech data associated with the telephone number of communication terminal 201-1 from the database 121. Then, the comparison means 131 compares the tone of the read speech data with the tone of the speech data transmitted from the communication terminal 201-1. As a result of the comparison, the comparison means 131 determines whether the difference between the tone of the read speech data and the tone of the speech data transmitted from the communication terminal 201-1 is outside the predetermined range (Step S15).

As a result of the comparison by the comparison means 131, when the comparison means 131 determines that the difference between the tone of the read speech data and the tone of the speech data transmitted from the communication terminal 201-1 is outside the predetermined range, the notification means 141 issues a predetermined notification to the communication terminal 201-2 (Step S16). Here, when the notification means 141 issues a notification using an e-mail, it reads the e-mail address of the communication terminal 201-2 associated with the communication terminal 201-1 from the database 121 and issues a notification to the read e-mail address as a destination. When the notification means 141 issues a notification using an SMS, it reads the telephone number of the communication terminal 201-2 associated with the communication terminal 201-1 from the database 121 and issues a notification to the read telephone number as a destination.

The communication terminal 201-2 that has received the notification from the management server 101 displays the received notification (Step S17). Here, when the notification transmitted from the management server 101 is one using an e-mail, the communication terminal 201-2 displays the notification by a method of receiving and displaying a usual e-mail. The same applies to the case when this notification is one using an SMS.

Figure 7:
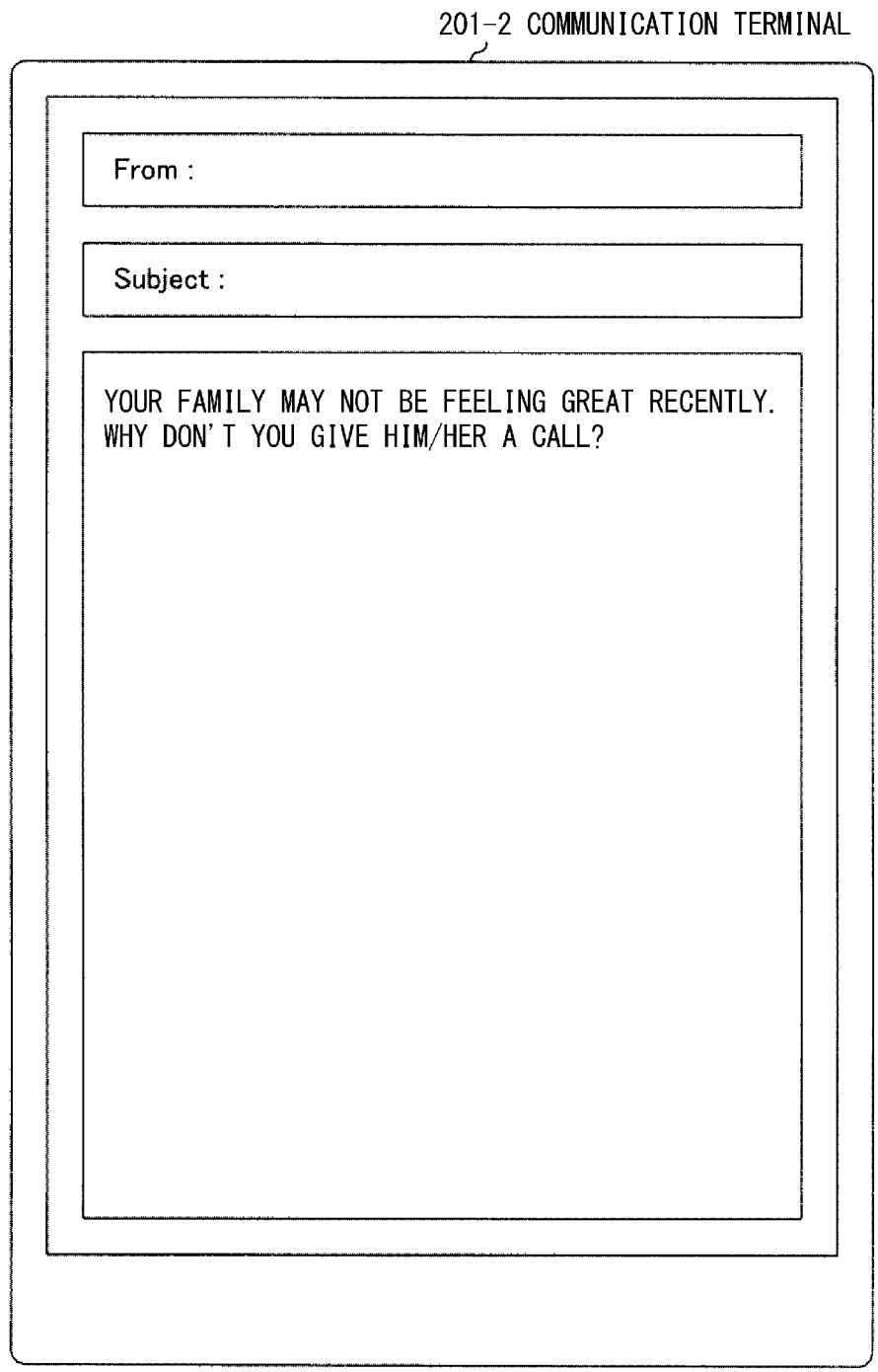
FIG. 7 is a diagram showing an example of a display mode in which a notification is displayed by a communication terminal shown in FIG. 3.

FIG. 7 is a diagram showing an example of a display mode in which the communication terminal 201-2 shown in FIG. 3 displays a notification. The example shown in FIG. 7 shows a display mode on the communication terminal 201-2 when the notification means 141 issues a notification using an e-mail. When the communication terminal 201-2 shown in FIG. 3 receives a notification using an e-mail from the management server 101, the communication terminal 201-2 displays the notification using an e-mail application. In the example shown in FIG. 7, the communication terminal 201-2 displays a notification of "Your family may not be feeling great recently. Why don't you give him/her a call?" using an e-mail application.

Figure 8:
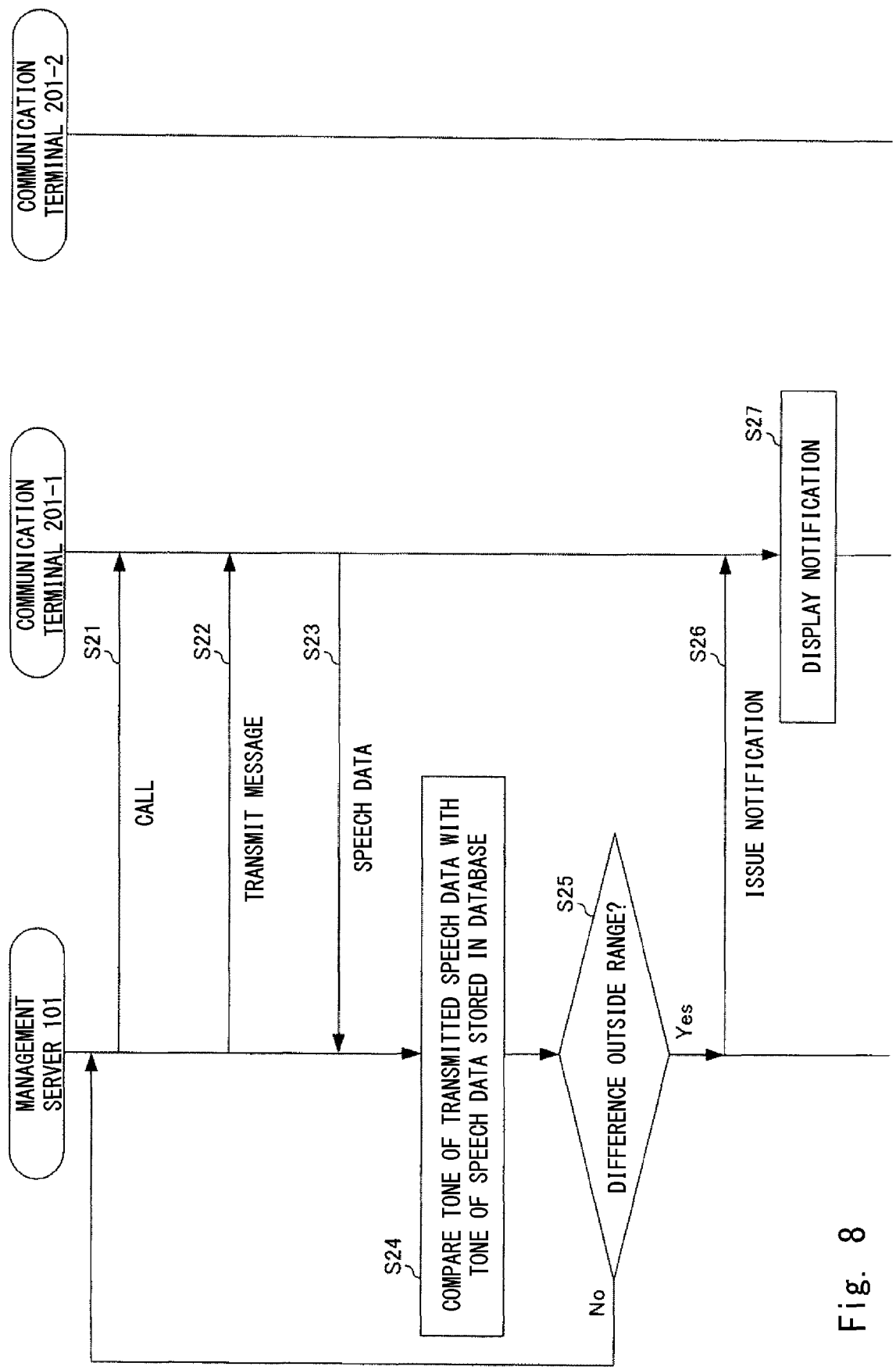
FIG. 8 is a sequence diagram for describing another example of a notification method in the notification system shown in FIG. 3.

FIG. 8 is a sequence diagram for describing another example of the notification method in the notification system shown in FIG. 3. Here, a case where the notification destination to which the notification means 141 shown in FIG. 4 issues a notification is the communication terminal 201-1 will be described as an example.

First, the calling means 111 makes a call to the communication terminal 201-1 possessed by the target person (Step S21). When the communication terminal 201-1 responds (is hooked off), the calling means 111 transmits a message (or guidance) to the communication terminal 201-1 (Step S22).

After that, when an owner of the communication terminal 201-1 speaks, the communication terminal 201-1 transmits the speech data to the management server 101 (Step S23).

When the speech data is transmitted from the communication terminal 201-1, the comparison means 131 compares the tone of the speech data transmitted from the communication terminal 201-1 with the tone of the speech data stored in the database 121 (Step S24). Specifically, the comparison means 131 reads the tone of the speech data associated with the telephone number of communication terminal 201-1 from the database 121. Then, the comparison means 131 compares the tone of the read speech data with the tone of the speech data transmitted from the communication terminal 201-1. As a result of the comparison, the comparison means 131 determines whether the difference between the tone of the read speech data with the tone of the speech data transmitted from the communication terminal 201-1 is outside the predetermined range (Step S25).

As a result of the comparison by the comparison means 131, when the comparison means 131 determines that the difference between the tone of the read speech data and the tone of the speech data transmitted from the communication terminal 201-1 is outside the predetermined range, the notification means 141 issues a predetermined notification to the communication terminal 201-1 (Step S26). Here, when the notification means 141 issues a notification using an e-mail, it reads the e-mail address of the communication terminal 201-1 from the database 121 and issues a notification to the read e-mail address as a destination. When the notification means 141 issues a notification using an SMS, it reads the telephone number of the communication terminal 201-1 from the database 121 and issues a notification to the read telephone number as a destination.

The communication terminal 201-1 that has received the notification from the management server 101 displays the received notification (Step S27). Here, when the notification transmitted from the management server 101 is one using an e-mail, the communication terminal 201-1 displays the notification by a method of receiving and displaying a usual e-mail. The same applies to the case when this notification is one using an SMS.

Figure 9:
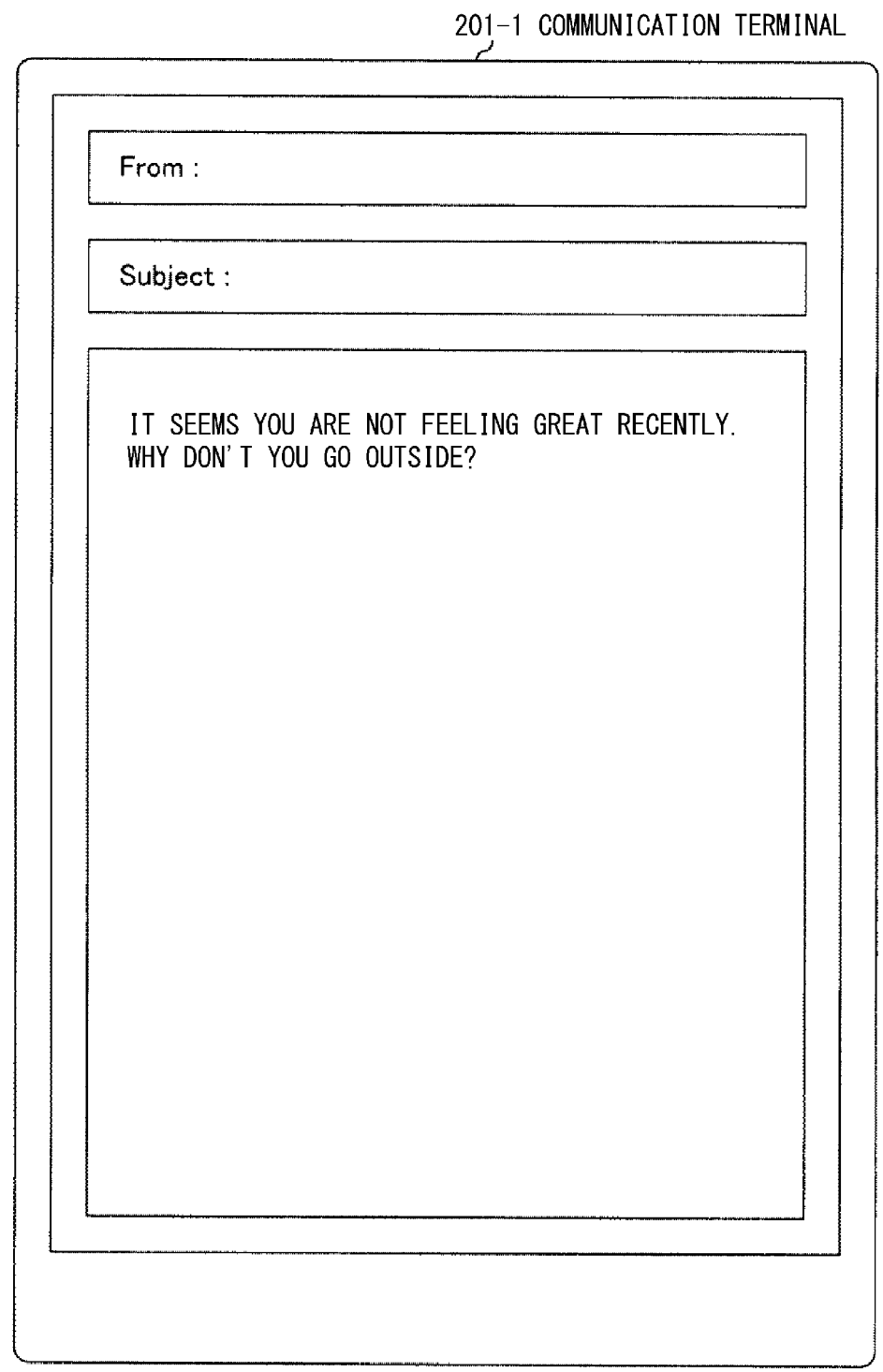
FIG. 9 is a diagram showing an example of a display mode in which a notification is displayed by the communication terminal possessed by a target person shown in FIG. 3.

FIG. 9 is a diagram showing an example of a display mode in which the communication terminal 201-1 shown in FIG. 3 displays a notification. The example shown in FIG. 9 shows a display mode on the communication terminal 201-1 when the notification means 141 issues a notification using an e-mail. When the communication terminal 201-1 shown in FIG. 3 receives a notification using an e-mail from the management server 101, the communication terminal 201-1 displays the notification using an e-mail application. In the example shown in FIG. 9, the communication terminal 201-1 displays a notification of "It seems you are not feeling great recently. Why don't you go outside?" using an e-mail application.

As described above, in this embodiment, the management server 101 transmits a message or guidance to the communication terminal 201-1. In regard to the message or guidance transmitted from the management server 101, the management server 101 compares the tone of the speech data transmitted from the communication terminal 201-1 with the tone of the speech data registered in advance. When the difference between the tone of the speech data transmitted from the communication terminal 201-1 and the tone of the speech data registered in advance is determined to be outside a predetermined range, the management server 101 issues a notification to the communication terminal 201-1 or the communication terminal 201-2. Therefore, in regard to the condition of the target person who possesses the communication terminal 201-1, the target person who possesses the communication terminal 201-1 or a family who possesses the communication terminal 201-2 can obtain correct information about the condition of the target person. When the difference between the tone of the speech data transmitted from the communication terminal 201-1 and the tone of the speech data registered in advance is within the predetermined range, the management server 101 does not issue a notification. By doing so, it is possible to prevent an increase in communication traffic caused by unnecessary notifications.

Third Embodiment

Figure 10:
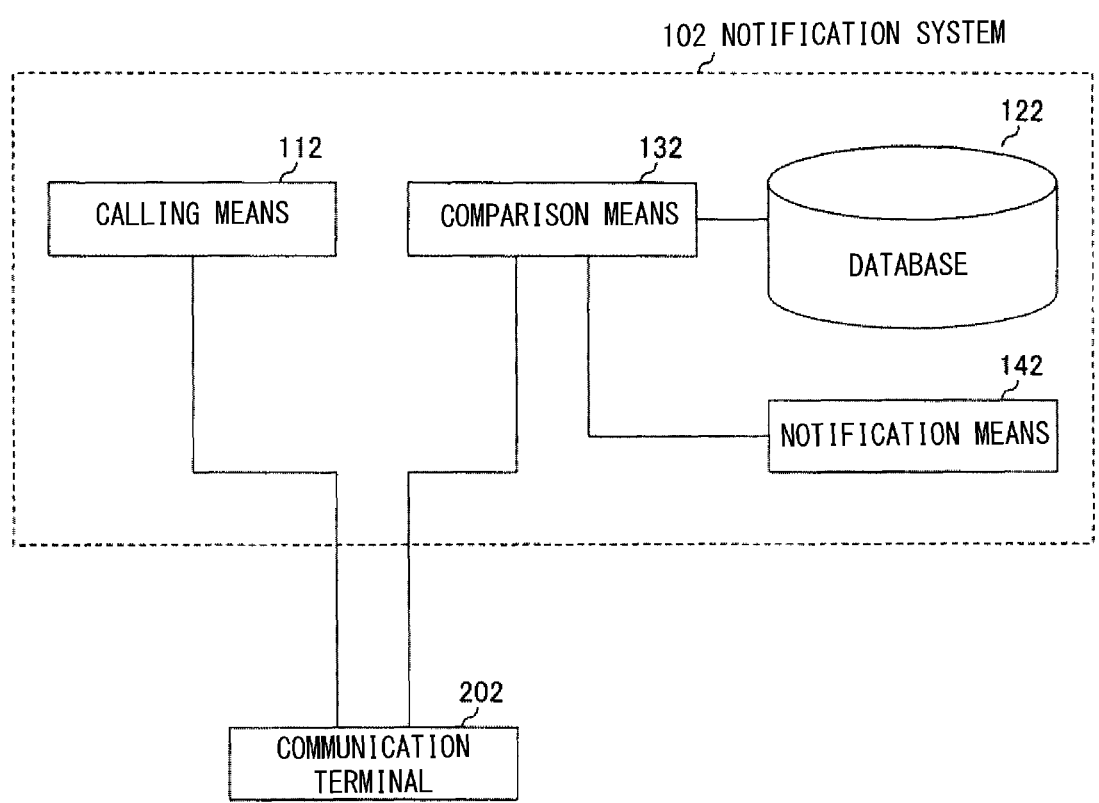
FIG. 10 is a diagram showing a third embodiment of a notification system according to the present disclosure.

FIG. 10 is a diagram showing a third embodiment of the notification system according to the present disclosure. As shown in FIG. 10, the notification system 102 according to this embodiment includes calling means 112, a database 122, comparison means 132, and notification means 142.

The calling means 112 makes a call to the communication terminal 202 possessed by the target person. The calling means 112 transmits a question to the communication terminal 202.

The database 122 stores in advance an answer that are predicted to be made by the target person in response to a question transmitted by the calling means 112.

The comparison means 132 compares an answer transmitted from the communication terminal 202 with the answer stored in the database 122.

The notification means 142 issues a predetermined notification when the answer transmitted from the communication terminal 202 does not match the responses stored in the database 122 as a result of the comparison by the comparison means 132.

Figure 11:
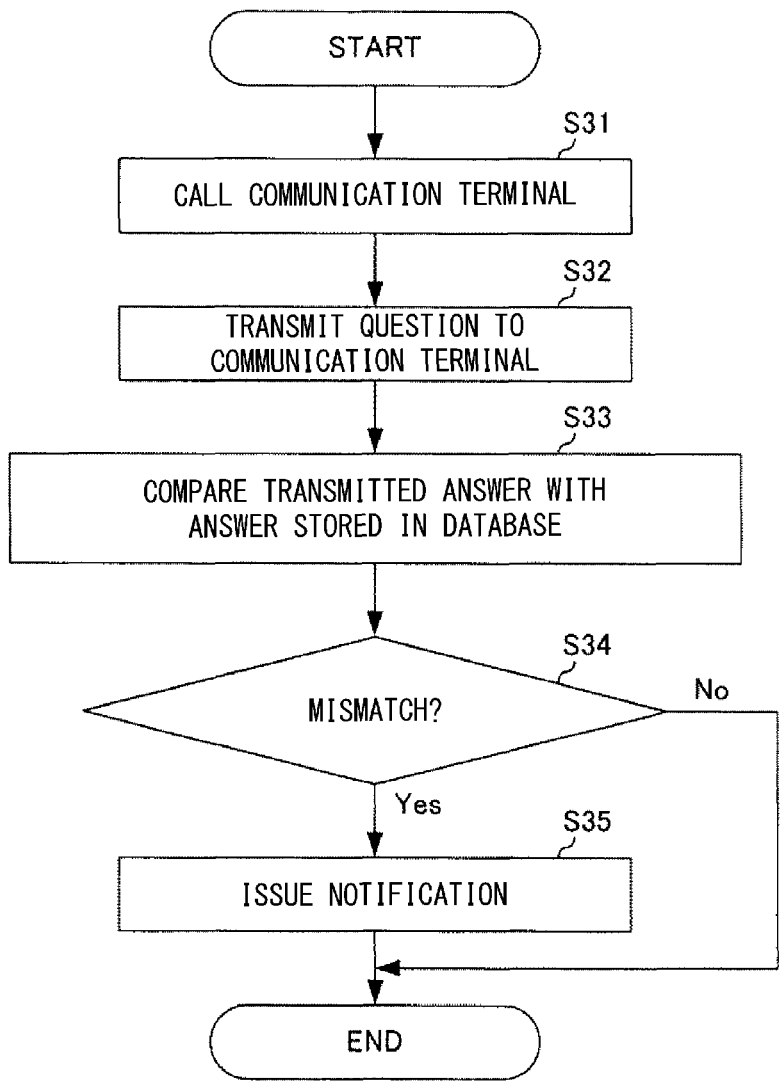
FIG. 11 is a flowchart for describing an example of a notification method in the notification system shown in FIG. 10.

A notification method in the notification system 102 shown in FIG. 10 will be described below. FIG. 11 is a flowchart for describing an example of the notification method in the notification system 102 shown in FIG. 10.

First, the calling means 112 makes a call to the communication terminal 202 possessed by the target person (Step S31). When the communication terminal 202 responds (is hooked off), the calling means 112 transmits a question to the communication terminal 202 (Step S32).

After that, when an answer is transmitted from the communication terminal 202, the comparison means 132 compares the answer transmitted from the communication terminal 202 with the answer stored in the database 122 (Step S33). As a result of the comparison, the comparison means 132 determines whether the answer transmitted from the communication terminal 202 and the answer stored in the database 122 are a mismatch (Step S34). When the answers are a mismatch as a result of the comparison by the comparison means 132, the notification means 142 issues a predetermined notification (Step S35).

As described above, the notification system 102 according to this embodiment issues a notification when the answer transmitted from the communication terminal 202 in response the question transmitted from the notification system 102 does not match the answer registered in advance. Thus, it is possible to obtain correct information about the condition of the target person who possesses the communication terminal 202.

Fourth Embodiment

Figure 12:
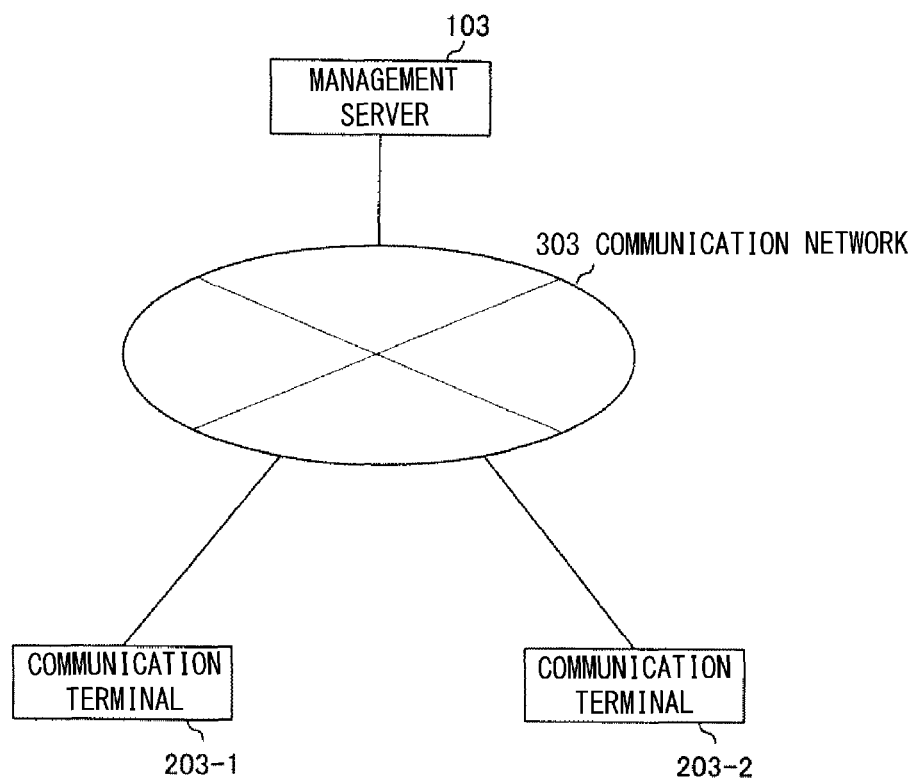
FIG. 12 is diagram showing a fourth embodiment of a notification system according to the present disclosure.

FIG. 12 is a diagram showing a fourth embodiment of the notification system according to the present disclosure. The notification system according to this embodiment is implemented by an apparatus of a management server 103. As shown in FIG. 12, this embodiment includes the management server 103 that is a notification system and communication terminals 203-1 and 203-2. The management server 103 is connected the communication terminals 203-1 and 203-2 via a communication network 303.

The communication terminal 203-1 is a communication apparatus such as a mobile terminal possessed by the target person. The communication terminal 203-2 is a communication apparatus such as a mobile terminal possessed by the target person's family or relatives. Telephone numbers and e-mail addresses of the communication terminals 203-1 and 203-2 are registered in advance in the management server 103 in association with the respective communication terminals 203-1 and 203-2.

Figure 13:
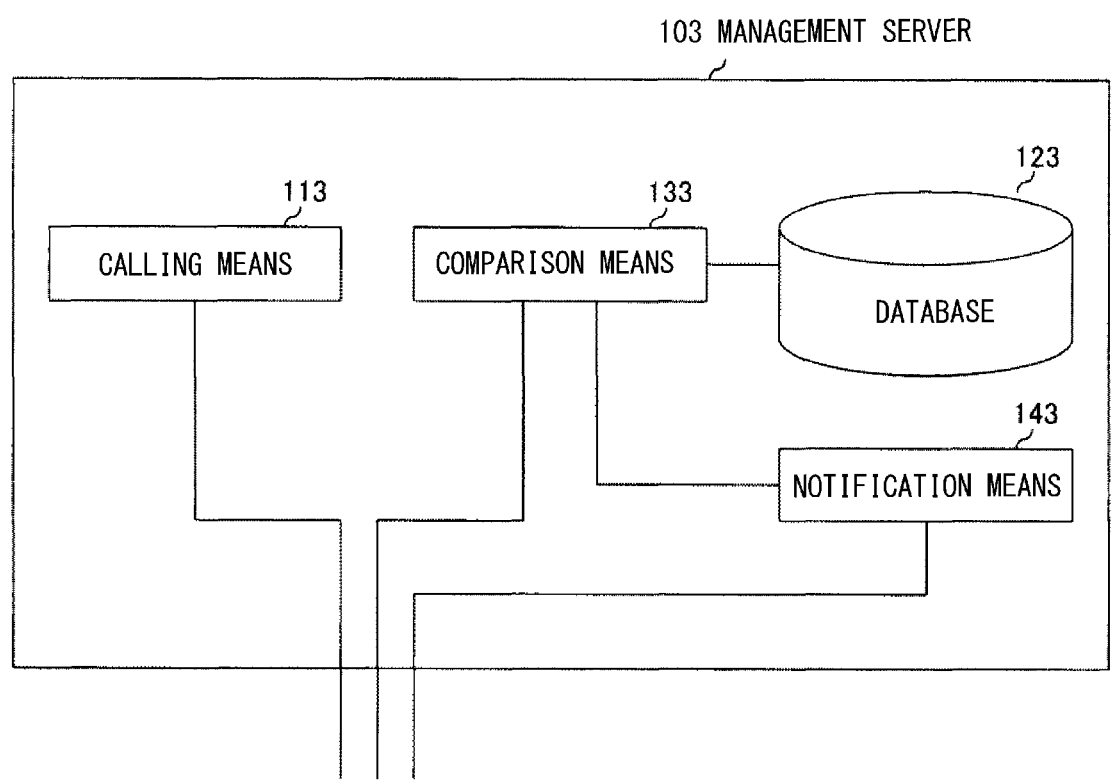
FIG. 13 is a diagram showing an example of an internal configuration of a management server shown in FIG. 12.

FIG. 13 is a diagram showing an example of an internal configuration of the management server 103 shown in FIG. 12. As shown in FIG. 13, the management server 103 shown in FIG. 12 includes calling means 113, a database 123, comparison means 133, and notification means 143. FIG. 13 shows an example of main components regarding this embodiment among the components included in the management server 103 shown in FIG. 12.

The calling means 113 makes a call to the communication terminal 203-1 possessed by the target person. When the communication terminal 203-1 responds after the calling means 113 makes a call to the communication terminal 203-1, the calling means 113 transmits a question to the communication terminal 203-1. This question is registered in advance in the database 123 in association with an answer to the question. For example, the question preferably has a known answer such as "What is your name?", "How many grandchildren do you have?", and "What did you have for dinner last night?". Note that this question preferably matches the target person's preference and may be stored in the database 123 in association with the target person in advance. By using the question associated with the target person, it is possible to prompt the target person to answer the question without making him/her bored.

The database 123 stores in advance questions and answers for the target person. The database 123 further stores in advance a telephone number and an e-mail address of the communication terminal 203-1 in association with a telephone number and an e-mail address of the communication terminal 203-2.

FIG. 14 is a diagram showing an example of an association between questions and answers stored in the database 123 shown in FIG. 13. As shown in FIG. 14, the database 123 shown in FIG. 13 stores a telephone number and an e-mail address of the target person in association with the questions and answers for the target person. Although a plurality of questions and answers are associated with one telephone number and one e-mail address here, one question and one answer may be associated with one telephone number and one e-mail address.

The comparison means 133 compares the answer transmitted from the communication terminal 203-1 with the answer stored in the database 123 in association with the question transmitted from the calling means 113 to the communication terminal 203-1. The comparison means 133 determines whether the answer transmitted from the communication terminal 203-1 with the answer stored in the database 123 in association with the question transmitted from the calling means 113 to the communication terminal 203-1 are a mismatch as a result of the comparison. For example, it is possible to detect that the target person gives an answer with a content different from a content that he/she can usually answer because of him/her feeling ill. Consequently, it is possible to recognize that the target person is feeling ill.

The notification means 143 issues a predetermined notification when the answer transmitted from the communication terminal 203-1 does not match the answer stored in the database 123 in association with the question transmitted from the calling means 113 to the communication terminal 203-1 as a result of the comparison by the comparison means 133. The notification means 143 issues this notification to the communication terminal 203-1. Alternatively, the notification means 143 issues this notification to the communication terminal 203-2. Further alternatively, the notification means 143 issues this notification to both the communication terminal 203-1 and the communication terminal 203-2. The notification means 143 may issue a notification using an e-mail, an SMS, or a voice call. Note that the notification means 143 may issue a notification when a mismatch determined from the result of the comparison by the comparison means 133 continues for a predetermined period such as a few days. A content of this notification indicates, for example, that the condition of the target person seems to be different from usual or suggests an action to be taken.

Figure 15:
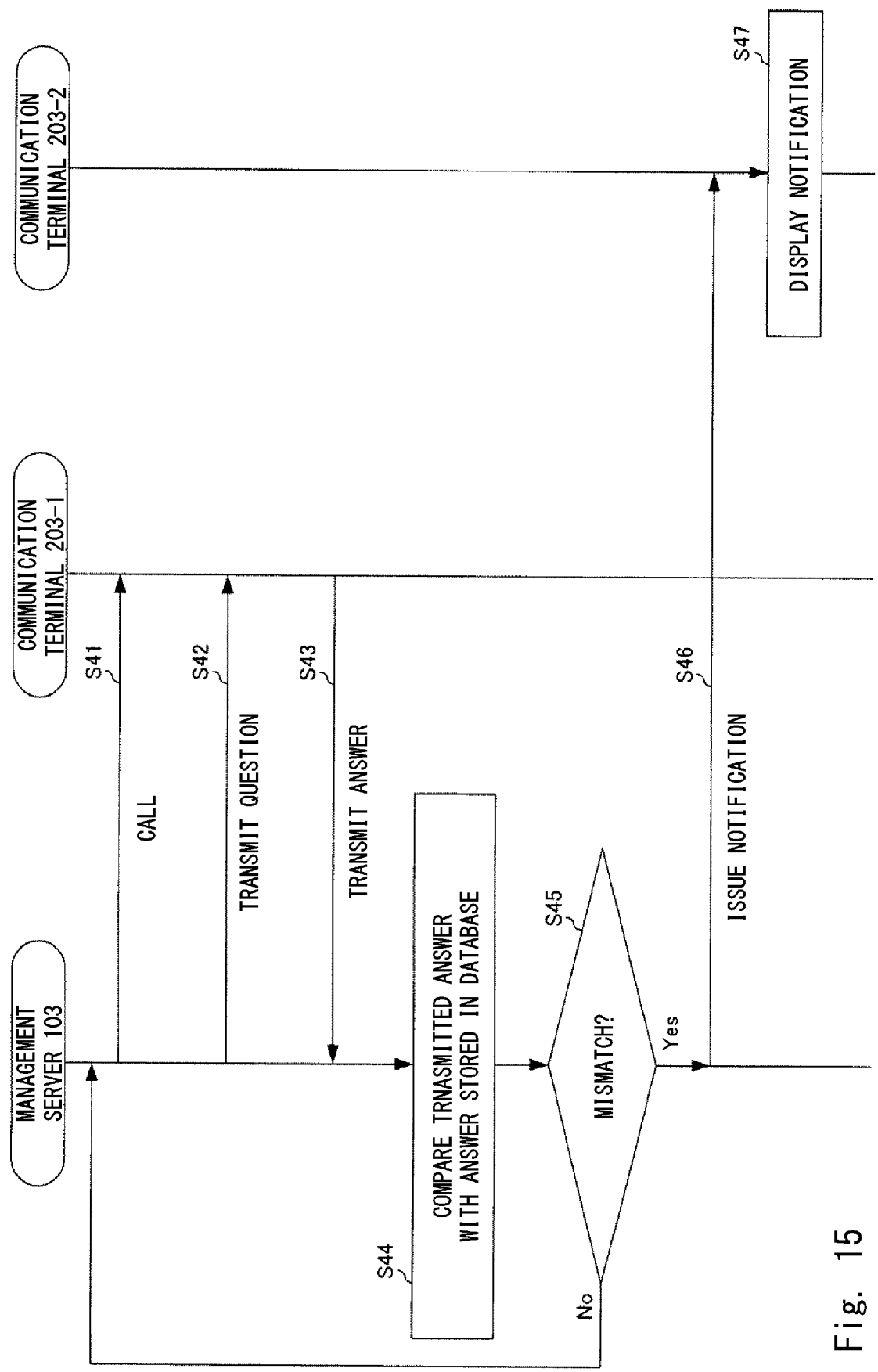
FIG. 15 is a sequence diagram for describing an example of a notification method in the notification system shown in FIG. 12.

The notification method in the notification system shown in FIG. 12 will be described below. FIG. 15 is a sequence diagram for describing an example of the notification method in the notification system shown in FIG. 12. Here, a case where a notification destination to which the notification means 143 shown in FIG. 13 issues a notification is the communication terminal 203-2 will be described as an example.

First, the calling means 113 makes a call to the communication terminal 203-1 possessed by the target person (Step S41). When the communication terminal 203-1 responds (is hooked off), the calling means 113 transmits a question stored in the database 123 in association with the communication terminal 203-1 to the communication terminal 203-1 (Step S42).

After that, when an owner of the communication terminal 203-1 inputs an answer to the question, the communication terminal 203-1 transmits the input answer to the management server 103 (Step S43). The input of the answer here may be a voice input or a text input.

When the answer is transmitted from the communication terminal 203-1, the comparison means 133 compares the answer transmitted from the communication terminal 203-1 with the answer stored in the database 123 in association with the question transmitted from the calling means 113 (Step S44). Then, the comparison means 133 determines whether the answer transmitted from the communication terminal 203-1 and the answer stored in the database 123 in association with the question transmitted from the calling means 113 are a mismatch as a result of the comparison (Step S45).

As a result of the comparison by the comparison means 133, when the comparison means 133 determines that the answer transmitted from the communication terminal 203-1 and the answer stored in the database 123 in association with the question transmitted from the calling means 113 are a mismatch, the notification means 143 issues a predetermined notification to the communication terminal 203-2 (Step S46). Here, when the notification means 143 issues a notification using an e-mail, it reads the e-mail address of the communication terminal 203-2 associated with the communication terminal 203-1 from the database 123 and issues a notification to the read e-mail address as a destination. When the notification means 143 issues a notification using an SMS, it reads the telephone number of the communication terminal 203-2 associated with the communication terminal 203-1 from the database 123 and issues a notification to the read telephone number as a destination.

The communication terminal 203-2 that has received the notification from the management server 103 displays the received notification (Step S47). Here, when the notification transmitted from the management server 103 is one using an e-mail, the communication terminal 203-2 displays the notification by a method of receiving and displaying a usual e-mail. The same applies to the case when this notification is one using an SMS.

Figure 16:
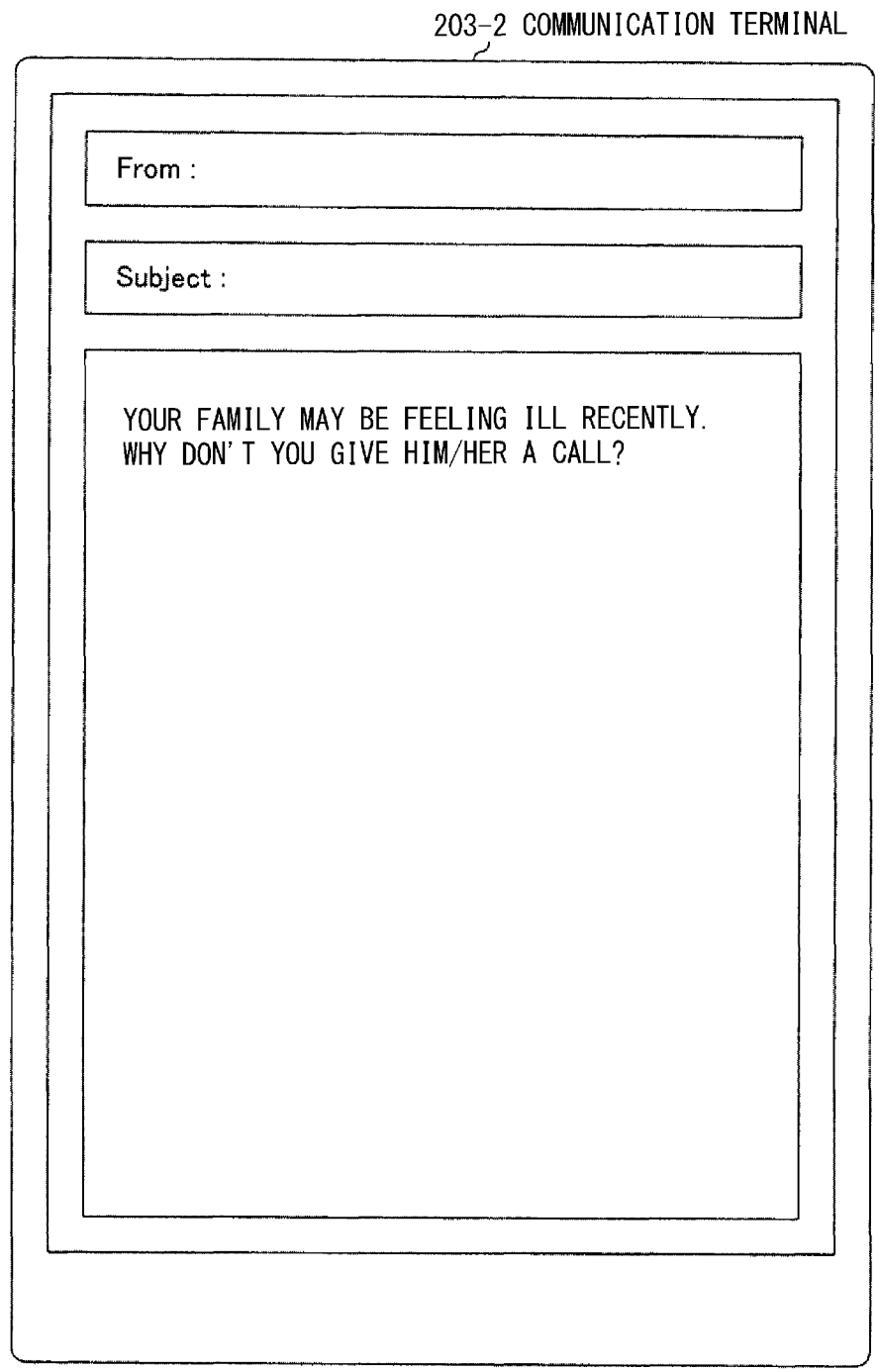
FIG. 16 is a diagram showing an example of a display mode in which a notification is displayed by a communication terminal shown in FIG. 12.

FIG. 16 is a diagram showing an example of a display mode in which the communication terminal 203-2 shown in FIG. 12 displays a notification. The example shown in FIG. 16 shows a display mode on the communication terminal 203-2 when the notification means 143 issues a notification using an e-mail. When the communication terminal 203-2 shown in FIG. 12 receives a notification using an e-mail from the management server 103, the communication terminal 203-2 displays the notification using an e-mail application. In the example shown in FIG. 16, the communication terminal 203-2 displays a notification of "Your family may be feeling ill recently. Why don't you give him/her a call?" using an e-mail application.

Figure 17:
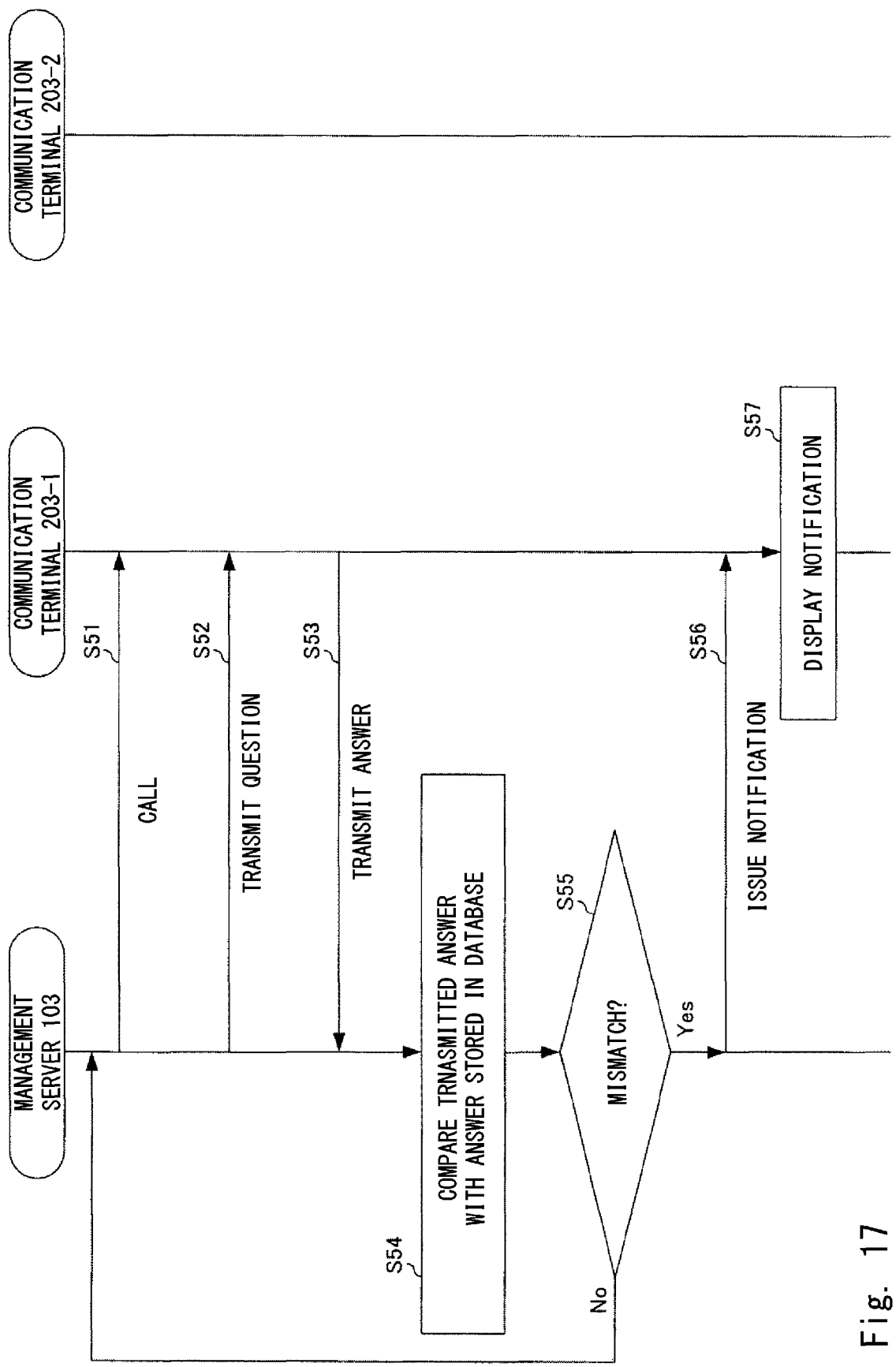
FIG. 17 is a sequence diagram for describing another example of the notification method in the notification system shown in FIG. 12.

FIG. 17 is a sequence diagram for describing another example of the notification method in the notification system shown in FIG. 12. Here, a case where the notification destination to which the notification means 143 shown in FIG. 13 issues a notification is the communication terminal 203-1 will be described as an example.

First, the calling means 113 makes a call to the communication terminal 203-1 possessed by the target person (Step S51). When the communication terminal 203-1 responds (is hooked off), the calling means 113 transmits a question stored in the database 123 in association with the communication terminal 203-1 to the communication terminal 203-1 (Step S52).

After that, when an owner of the communication terminal 203-1 inputs an answer to the question, the communication terminal 203-1 transmits the input answer to the management server 103 (Step S53). The input of the answer here may be a voice input or a text input.

When the answer is transmitted from the communication terminal 203-1, the comparison means 133 compares the answer transmitted from the communication terminal 203-1 with the answer stored in the database 123 in association with the question transmitted from the calling means 113 (Step S54). Then, the comparison means 133 determines whether the answer transmitted from the communication terminal 203-1 and the answer stored in the database 123 in association with the question transmitted from the calling means 113 are a mismatch as a result of the comparison (Step S55).

As a result of the comparison by the comparison means 133, when the comparison means 133 determines that the answer transmitted from the communication terminal 203-1 and the answer stored in the database 123 in association with the question transmitted from the calling means 113 are a mismatch, the notification means 143 issues a predetermined notification to the communication terminal 203-1 (Step S56). When the notification means 143 issues a notification using an e-mail, it reads the e-mail address of the communication terminal 203-1 from the database 123 and issues a notification to the read e-mail address as a destination. When the notification means 143 issues a notification using an SMS, it reads the telephone number of the communication terminal 203-1 from the database 123 and issues a notification to the read telephone number as a destination.

The communication terminal 203-1 that has received the notification from the management server 103 displays the received notification (Step S57). Here, when the notification transmitted from the management server 103 is one using an e-mail, the communication terminal 203-1 displays the notification by a method of receiving and displaying a usual e-mail. The same applies to the case when this notification is one using an SMS.

Figure 18:
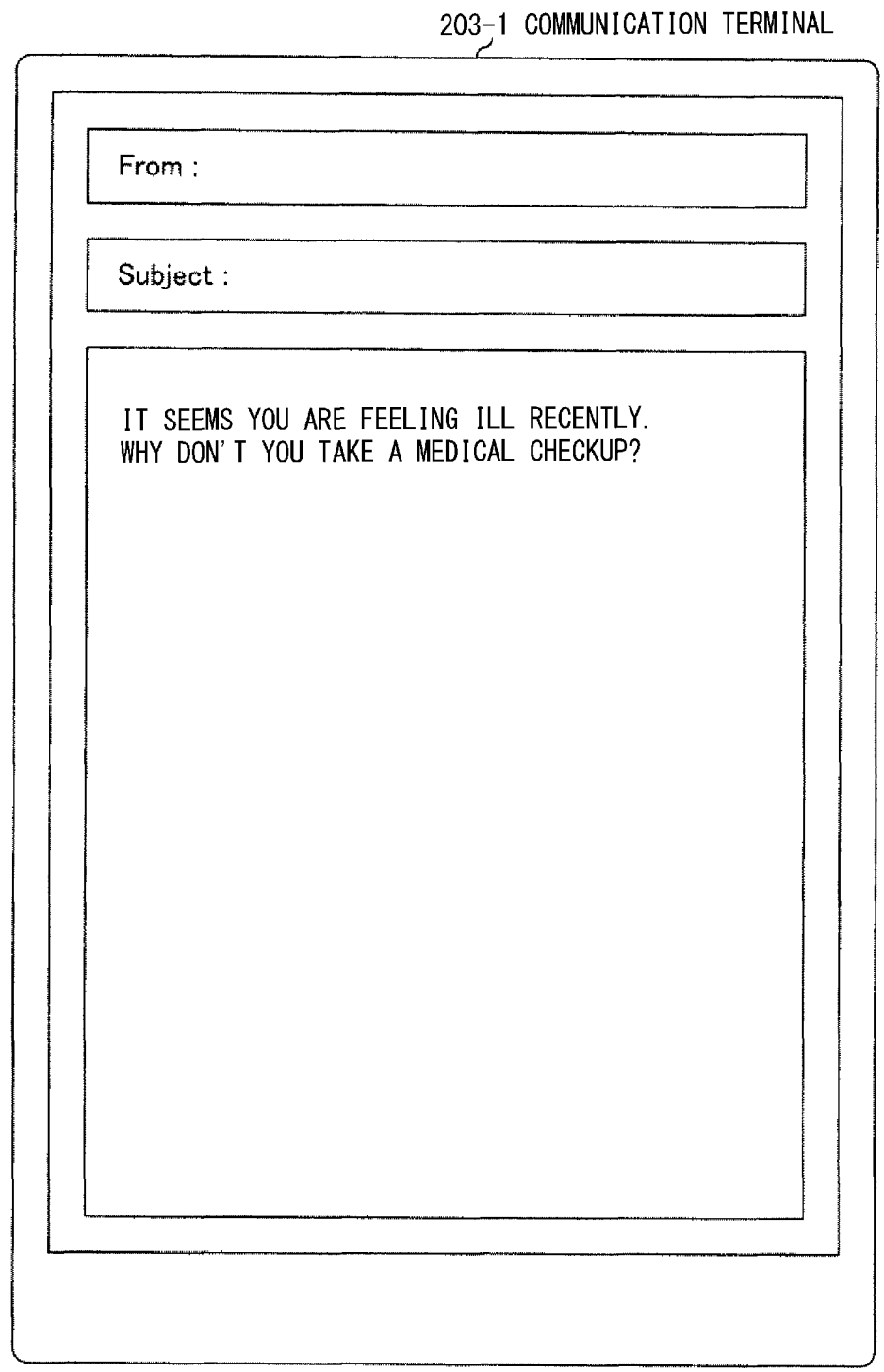
FIG. 18 is a diagram showing an example of a display mode in which a notification is displayed by the communication terminal possessed by the target person shown in FIG. 12.

FIG. 18 is a diagram showing an example of a display mode in which the communication terminal 203-1 shown in FIG. 12 displays a notification. The example shown in FIG. 18 shows a display mode on the communication terminal 203-1 when the notification means 143 issues a notification using an e-mail. When the communication terminal 203-1 shown in FIG. 12 receives a notification using an e-mail from the management server 103, the communication terminal 203-1 displays the notification using an e-mail application. In the example shown in FIG. 18, the communication terminal 203-1 displays a notification of "It seems you are feeling ill recently. Why don't you take a medical checkup?" using an e-mail application.

As described above, in this embodiment, the management server 103 transmits a question associated with the target person to the communication terminal 203-1. The management server 103 compares the answer transmitted from the communication terminal 203-1 in response to the question transmitted from the management server 103 with the answer registered in advance in association with this question. When the answer transmitted from the communication terminal 203-1 in response to the question transmitted from the management server 103 and the answer registered in advance in association with this question are a mismatch, the management server 103 transmits a notification to the communication terminal 203-1 or the communication terminal 203-2. Therefore, the target person who possesses the communication terminal 203-1 or the family who possesses the communication terminal 203-2 can obtain correct information about the condition of the target person who possesses the communication terminal 203-1. Further, when the answer transmitted from the communication terminal 203-1 matches the answer registered in advance, the management server 103 does not issue a notification. By doing so, it is possible to prevent an increase in communication traffic caused by unnecessary notifications.

Fifth Embodiment

Figure 19:
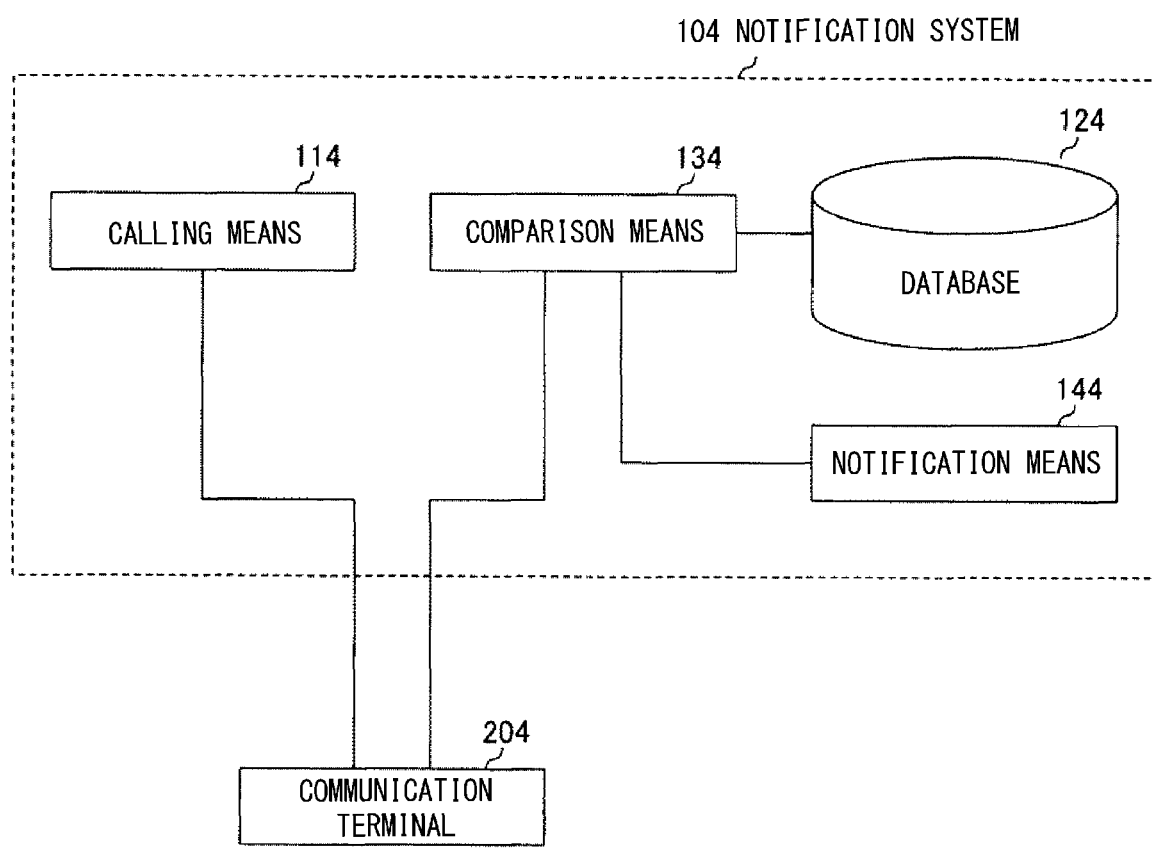
FIG. 19 is a diagram showing a fifth embodiment of the notification system according to the present disclosure.

FIG. 19 is a diagram showing a fifth embodiment of the notification system according to the present disclosure. As shown in FIG. 19, a notification system 104 according to this embodiment includes calling means 114, a database 124, comparison means 134, and notification means 144.

The calling means 114 makes a call to a communication terminal 204 possessed by the target person.

The database 124 stores in advance an operation method for the target person to operate the communication terminal 204.

The comparison means 134 compares an operation method of the communication terminal 204 performed by the target person with the operation method stored in the database 124.

When the operation method of the communication terminal 204 performed by the target person is determined to be outside a predetermined range as a result of the comparison by the comparison means 134, the notification means 144 issues a predetermined notification.

Figure 20:
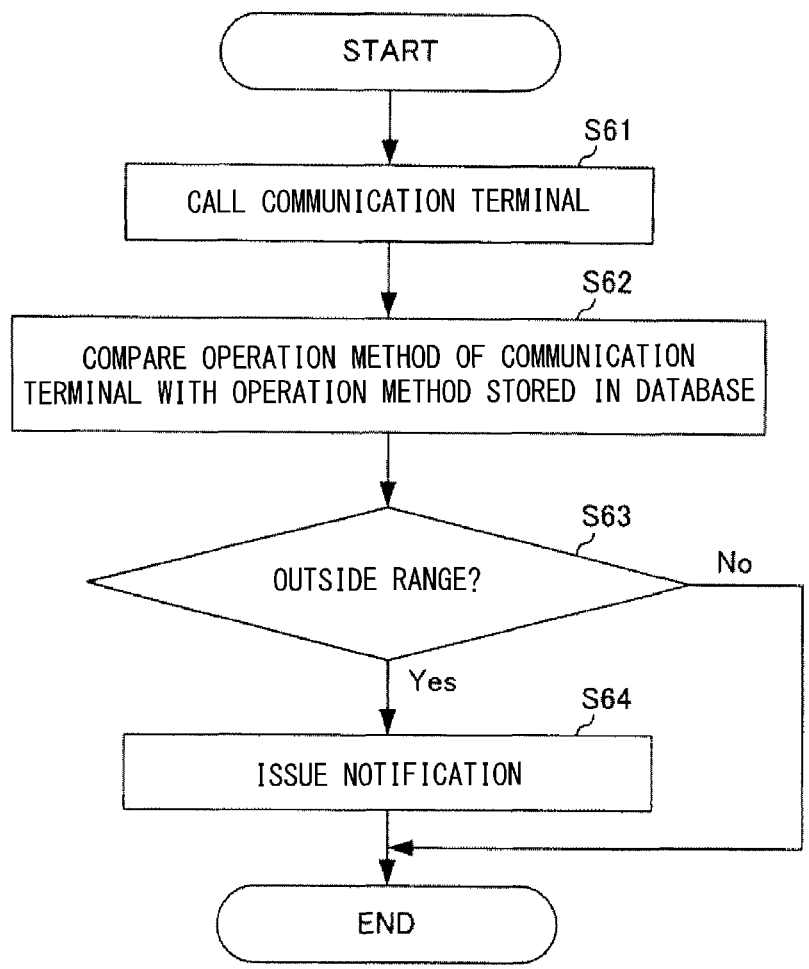
FIG. 20 is a flowchart for describing an example of a notification method in the notification system shown in FIG. 19.

A notification method in the notification system 104 shown in FIG. 19 will be described below. FIG. 20 is a flowchart for describing an example of the notification method in the notification system 104 shown in FIG. 19.

First, the calling means 114 makes a call to the communication terminal 204 possessed by the target person (Step S61). After that, the comparison means 134 compares the operation method of the communication terminal 204 which was performed by the target person with the operation method stored in the database 124 (Step S62). The comparison means 134 determines whether the operation method of the communication terminal 204 which was performed by the target person is outside the predetermined range as a result of the comparison (Step S63). As a result of the comparison by the comparison means 134, when the operation method of the communication terminal 204 which was performed by the target person is determined to be outside the predetermined range, the notification means 144 issues a predetermined notification (Step S64).

In this manner, the notification system 104 according to this embodiment issues a notification when the operation method of the communication terminal 204 which was performed by the target person is determined to be outside the predetermined range stored in the database 124. Thus, it is possible to obtain correct information about the condition of the target person who possesses the communication terminal 204.

Sixth Embodiment

Figure 21:
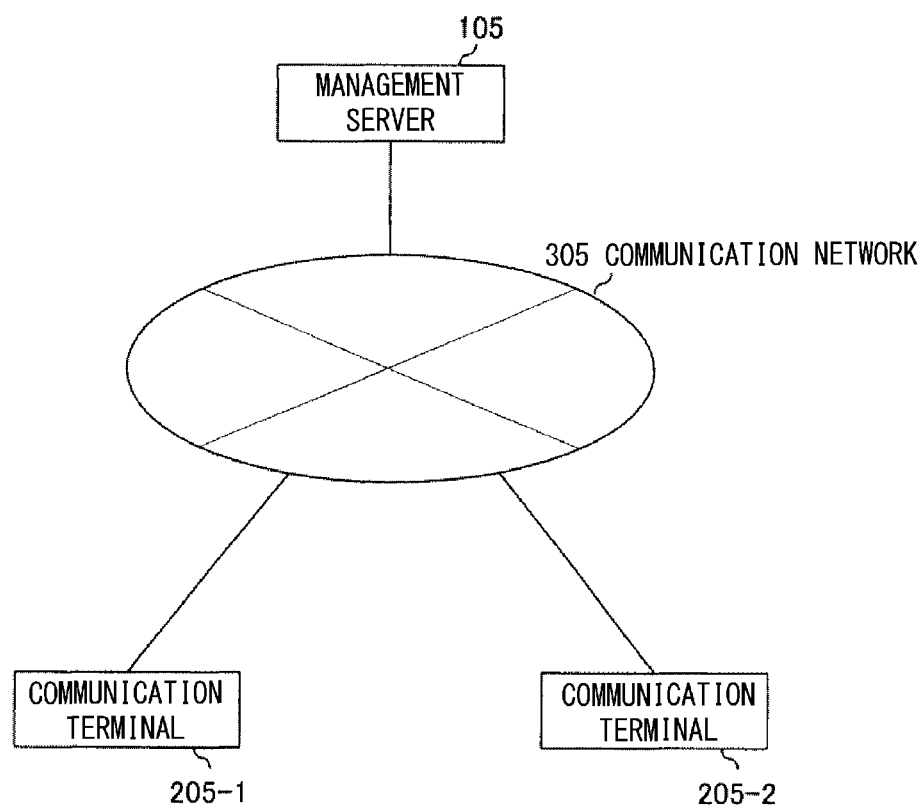
FIG. 21 is a diagram showing a sixth embodiment of a notification system according to the present disclosure.

FIG. 21 is a diagram showing a sixth embodiment of the notification system according to the present disclosure. The notification system according to this embodiment is implemented by an apparatus of a management server 105. As shown in FIG. 21, this embodiment includes the management server 105 that is a notification system and communication terminals 205-1 and 205-2. The management server 105 is connected the communication terminals 205-1 and 205-2 via a communication network 305.

The communication terminal 205-1 is a communication apparatus such as a mobile terminal possessed by the target person. The communication terminal 205-2 is a communication apparatus such as a mobile terminal possessed by the target person's family or relatives. Telephone numbers and e-mail addresses of the communication terminals 205-1 and 205-2 are registered in advance in the management server 105 in association with the respective communication terminals 205-1 and 205-2.

Figure 22:
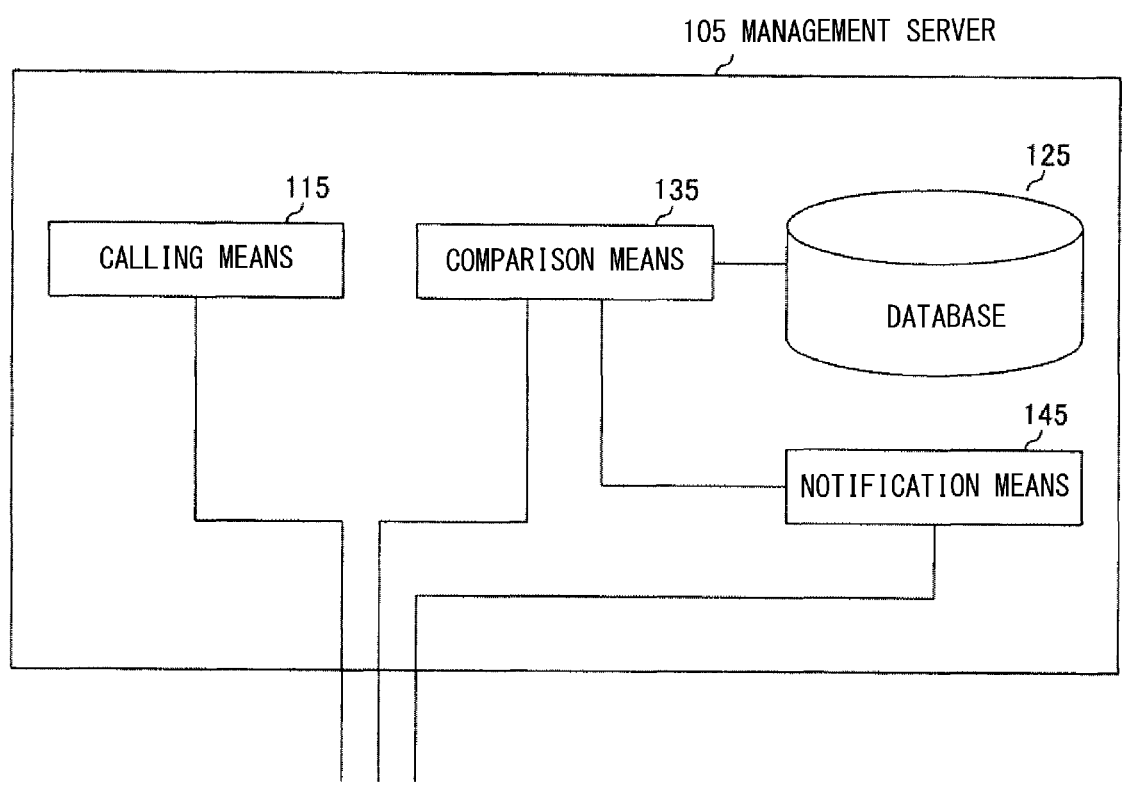
FIG. 22 is a diagram showing an example of an internal configuration of a management server shown in FIG. 21.

FIG. 22 is a diagram showing an example of an internal configuration of the management server 105 shown in FIG. 21. As shown in FIG. 22, the management server 105 shown in FIG. 21 includes calling means 115, a database 125, comparison means 135, and notification means 145. FIG. 22 shows an example of main components regarding this embodiment among the components included in the management server 105 shown in FIG. 21.

The calling means 115 makes a call to the communication terminal 205-1 possessed by the target person.

The database 125 stores in advance the operation method of the communication terminal performed by the target person. The database 125 stores a telephone number and an e-mail address of the communication terminal 205-1 and the operation method in association with each other in advance. The database 125 further stores in advance the telephone number and the e-mail address of the communication terminal 205-1 in association with a telephone number and an e-mail address of the communication terminal 205-2.

FIG. 23 is a diagram showing an example of the operation method of the communication terminal stored in the database 125 shown in FIG. 22. As shown in FIG. 23, the database 125 shown in FIG. 22 stores operation items and operation ranges, which are the operation method in association with a telephone number and an e-mail address of the target person. The operation item is an item for the target person to operate the communication terminal 205-1. As shown in FIG. 23, the operation items are, for example, a time from when a call is made until the call is answered, a time from when a call is answered until when the call is ended, and a time from when the management server 105 transmits a question during the a until the communication terminal 205-1 transmits an answer. The operation range is a range calculated based on an operation performed by the target person in a usual state for each operation item and is a reference for the comparison means 135 to determine whether the notification means 145 issues a notification.

The comparison means 135 compares the operation method of communication terminal 205-1 which was performed by the target person with the operation method stored in database 125 in association with the communication terminal 205-1 (operation range in the example shown in FIG. 23). The comparison means 135 determines whether the operation method of the communication terminal 205-1 which was performed by the target person is outside the operation range stored in the database 125 as a result of the comparison. By doing so, for example, it is possible to detect that the operation method by the target person exceeds the usual operation method because of him/her feeling ill. Consequently, it is possible to recognize that the target person is feeling ill.

When the operation method of the communication terminal 205-1 which was performed by the target person is determined to be outside the range of the operation range stored in the database 125 as a result of the comparison by the comparison means 135, the notification means 145 issues a predetermined notification. The notification means 145 issues this notification to the communication terminal 205-1. Alternatively, the notification means 145 issues this notification to the communication terminal 205-2. Further alternatively, the notification means 145 issues this notification to both the communication terminal 205-1 and the communication terminal 205-2. The notification means 145 may issue a notification using an e-mail, an SMS, or a voice call. Note that the notification means 145 may issue a notification when a state in which the operation method of the communication terminal 205-1 which was performed by the target person is determined to be outside the operation range stored in the database 125 as a result of the comparison by the comparison means 135 continues for a predetermined period such as a few days. A content of this notification indicates, for example, that the condition of the target person seems to be different from usual or suggests an action to be taken.

Figure 24:
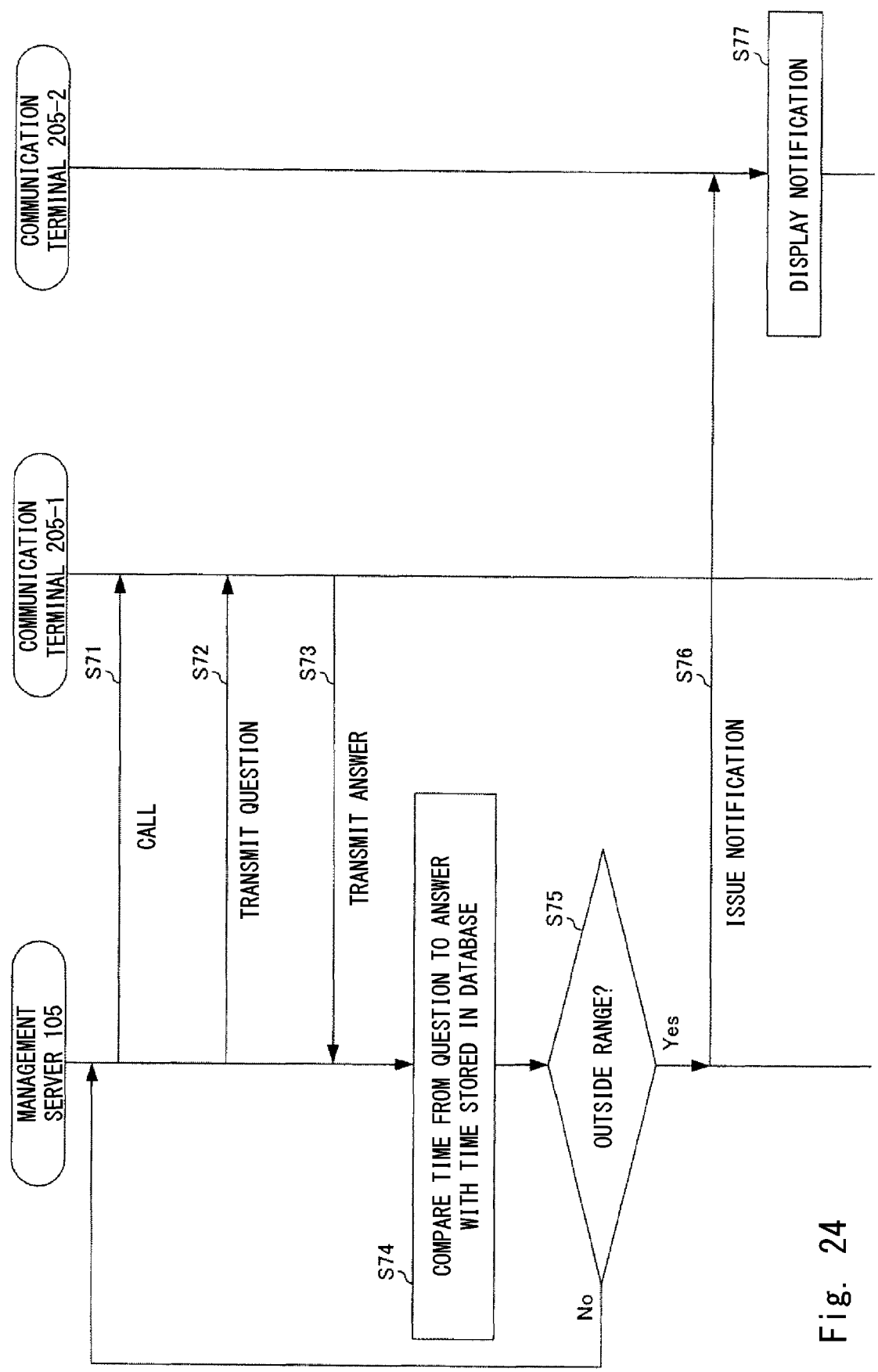
FIG. 24 is a sequence diagram for describing an example of a notification method in the notification system shown in FIG. 21.

The notification method in the notification system shown in FIG. 21 will be described below. FIG. 24 is a sequence diagram for describing an example of the notification method in the notification system shown in FIG. 21. Here, a case where a notification destination to which the notification means 145 shown in FIG. 22 issues a notification is the communication terminal 205-2 will be described as an example. Further, an example in which the operation method to be compared by the comparison means 135 shown in FIG. 22 is a time from when a question is transmitted until an answer is transmitted is described as an example.

First, the calling means 115 makes a call to the communication terminal 205-1 possessed by the target person (Step S71). When the communication terminal 205-1 responds (is hooked off), the calling means 115 transmits a question to the communication terminal 205-1 (Step S72). This question may be stored in the database 125 in association with the communication terminal 205-1.

After that, when an owner of the communication terminal 205-1 inputs an answer to the question, the communication terminal 205-1 transmits the input answer to the management server 105 (Step S73).

When the answer is transmitted from the communication terminal 205-1, the comparison means 135 compares a time from when the calling means 115 transmits a question until an answer is transmitted from the communication terminal 205-1 with the time stored in the database 125 as the operation method (operation range) (Step S74). Then, the comparison means 135 determines whether the time from when the calling means 115 transmits the question until when the answer is transmitted from the communication terminal 205-1 is outside the range of the operation range stored in the database 125 as the operation method (Step S75). When the comparison means 135 determines that the time from when the calling means 115 transmits the question until when the answer is transmitted from the communication terminal 205-1 is determined to be outside the range of the operation range stored in the database 125 as the operation method as a result of the comparison by the comparison means 135, the notification means 145 issues a predetermined notification to the communication terminal 205-2 (Step S76). Here, when the notification means 145 issues a notification using an e-mail, it reads the e-mail address of the communication terminal 205-2 associated with the communication terminal 205-1 from the database 125 and issues a notification to the read e-mail address as a destination. When the notification means 145 issues a notification using an SMS, it reads a telephone number of the communication terminal 205-2 associated with the communication terminal 205-1 from the database 125 and issues a notification to the read telephone number as a destination.

The communication terminal 205-2 that has received the notification from the management server 105 displays the received notification (Step S77). Here, when the notification transmitted from the management server 105 is one using an e-mail, the communication terminal 205-2 displays the notification by a method of receiving and displaying a usual e-mail. The same applies to the case when this notification is one using an SMS.

Figure 25:
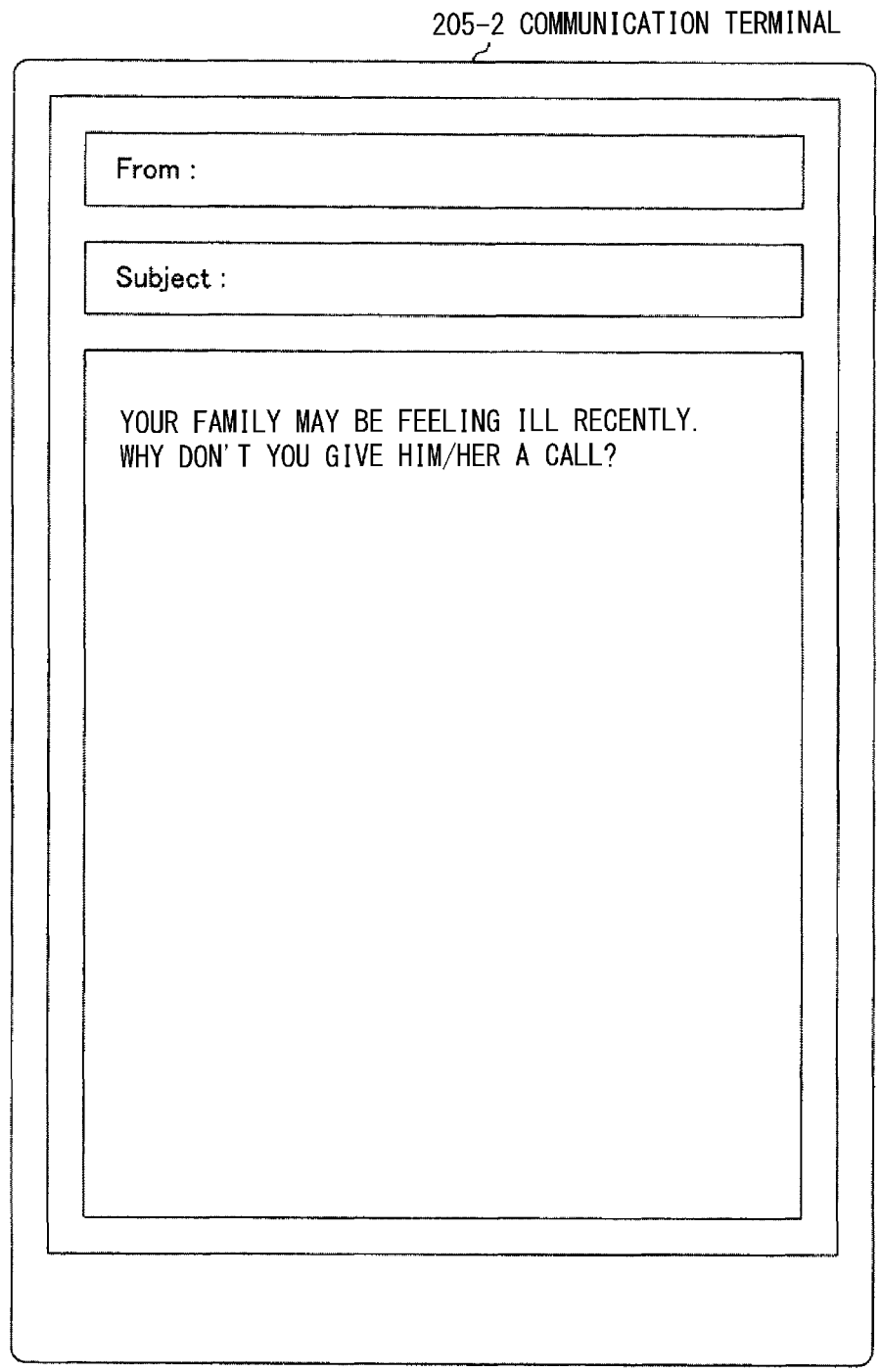
FIG. 25 is a diagram showing an example of a display mode in which notification is displayed by the communication terminal shown in FIG. 21

FIG. 25 is a diagram showing an example of a display mode in which the communication terminal 205-2 shown in FIG. 21 displays a notification. The example shown in FIG. 25 shows a display mode on the communication terminal 205-2 when the notification means 145 issues a notification using an e-mail. When the communication terminal 205-2 shown in FIG. 25 receives a notification using an e-mail from the management server 105, the communication terminal 205-2 displays the notification using an e-mail application. In the example shown in FIG. 25, the communication terminal 205-2 displays a notification of "Your family may be feeling ill recently. Why don't you give him/her a call?" using an e-mail application.

Figure 26:
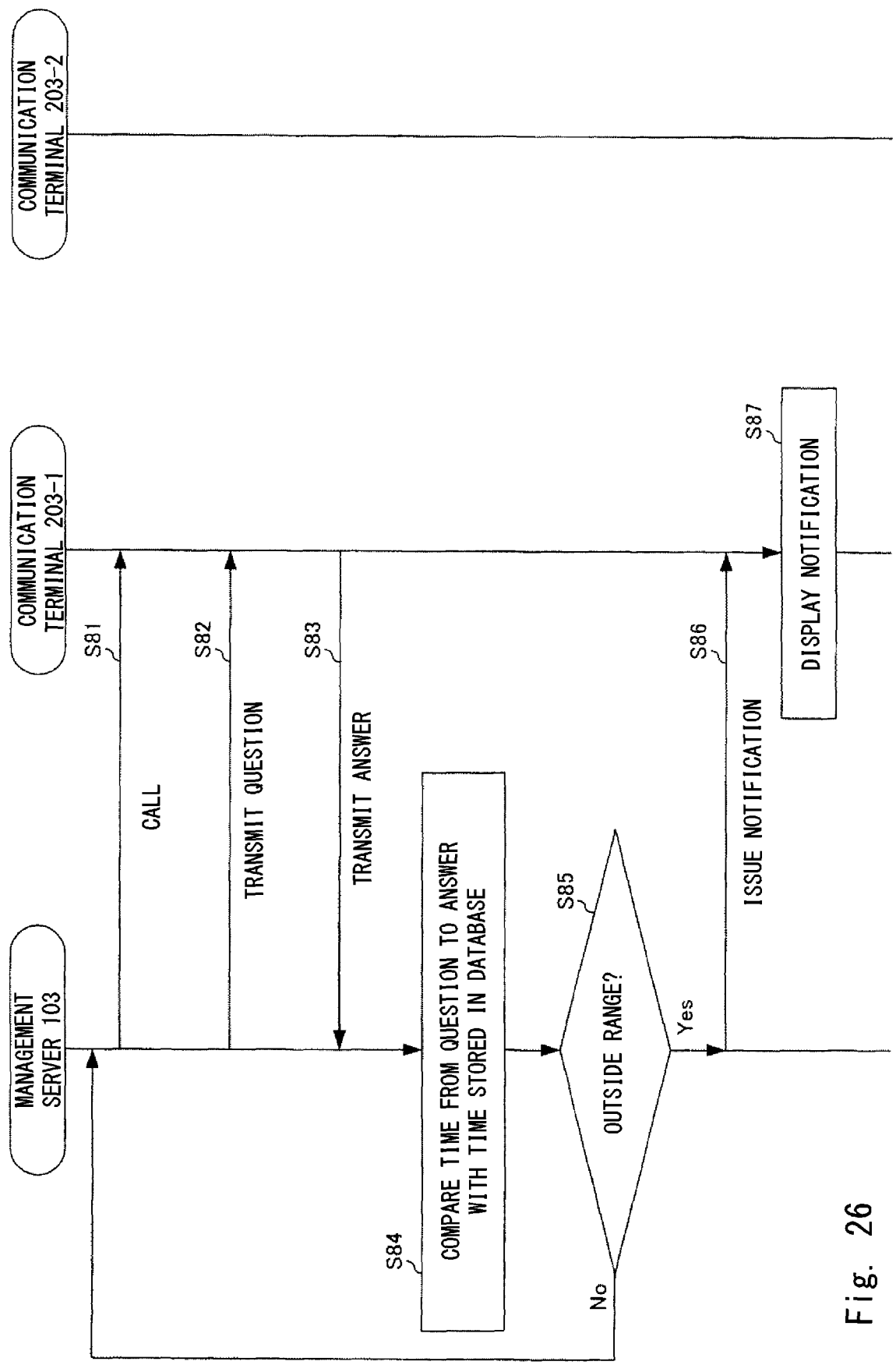
FIG. 26 is a sequence diagram for describing another example of the notification method in the notification system shown in FIG. 21.

FIG. 26 is a sequence diagram for describing another example of the notification method in the notification system shown in FIG. 21. Here, a case where the notification destination to which the notification means 145 shown in FIG. 22 issues a notification is the communication terminal 205-1 will be described as an example.

First, the calling means 115 makes a call to the communication terminal 205-1 possessed by the target person (Step S81). When the communication terminal 205-1 responds (is hooked off), the calling means 115 transmits a question to the communication terminal 205-1 (Step S82). This question may be stored in the database 125 in association with the communication terminal 205-1.

After that, when an owner of the communication terminal 205-1 inputs an answer to the question, the communication terminal 205-1 transmits the input answer to the management server 105 (Step S83).

When the answer is transmitted from the communication terminal 205-1, the comparison means 135 compares a time from when the calling means 115 transmits a question until an answer is transmitted from the communication terminal 205-1 with the time stored in the database 125 as the operation method (operation range) (Step S84). Then, the comparison means 135 determines whether the time from when the calling means 115 transmits the question until when the answer is transmitted from the communication terminal 205-1 is outside the range of the operation range stored in the database 125 as the operation method (Step S85).

When the comparison means 135 determines that the time from when the calling means 115 transmits the question until when the answer is transmitted from the communication terminal 205-1 is outside the range of the operation range stored in the database 125 as the operation method as a result of the comparison by the comparison means 135, the notification means 145 issues a predetermined notification to the communication terminal 205-1 (Step S86). When the notification means 145 issues a notification using an e-mail, it reads the e-mail address of the communication terminal 205-1 from the database 125 and issues a notification to the read e-mail address as a destination. When the notification means 145 issues a notification using an SMS, it reads the telephone number of the communication terminal 205-1 from the database 125 and issues a notification to the read telephone number as a destination.

The communication terminal 205-1 that has received the notification from the management server 105 displays the received notification (Step S87). Here, when the notification transmitted from the management server 105 is one using an e-mail, the communication terminal 205-1 displays the notification by a method of receiving and displaying a usual e-mail. The same applies to the case when this notification is one using an SMS.

Figure 27:
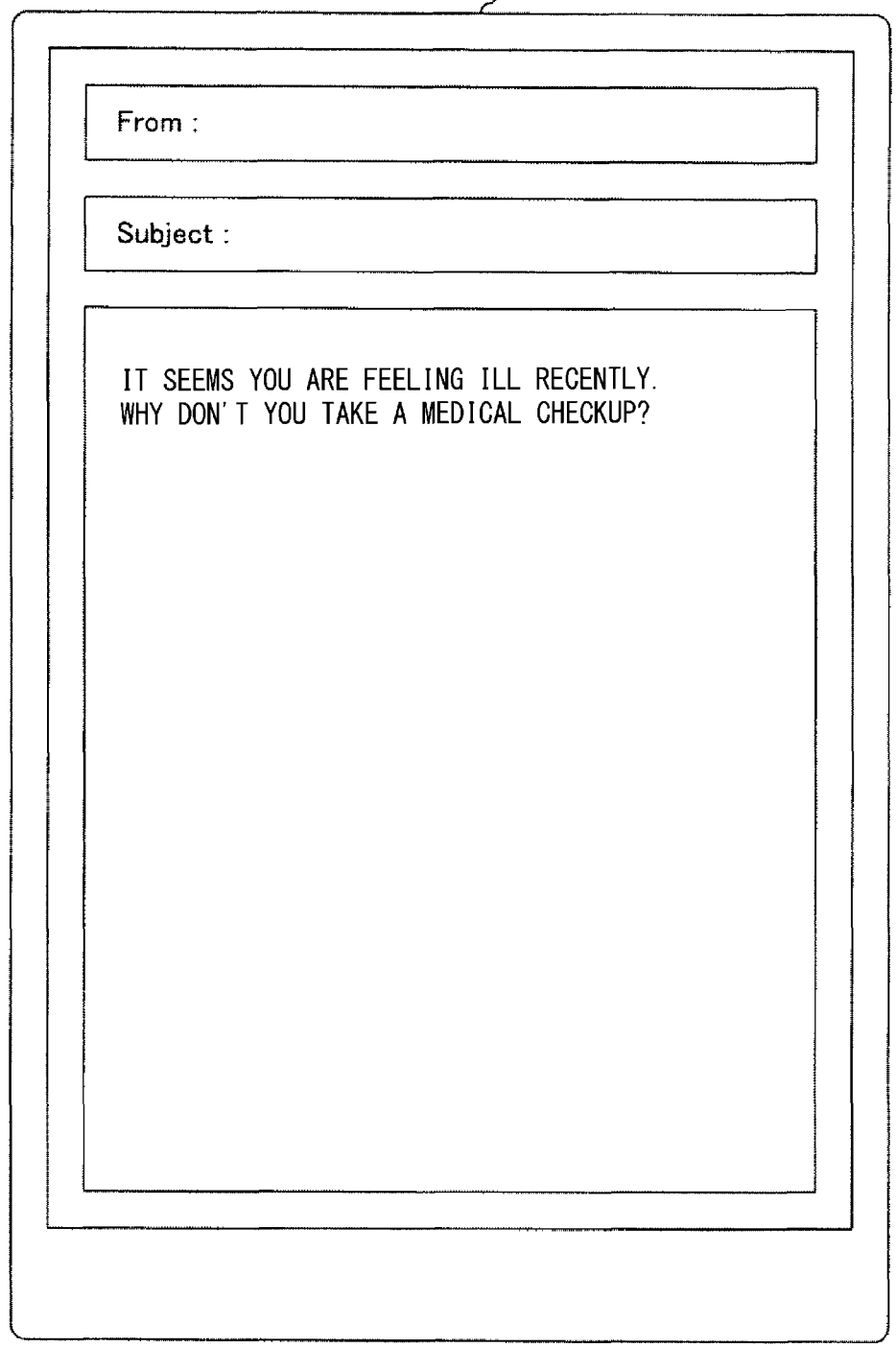
FIG. 27 is a diagram showing an example of a display mode in which a notification is displayed by a communication terminal possessed by a target person shown in FIG. 21.

FIG. 27 is a diagram showing an example of a display mode in which the communication terminal 203-1 shown in FIG. 21 displays a notification. The example shown in FIG. 27 shows a display mode on the communication terminal 205-1 when the notification means 145 issues a notification using an e-mail. When the communication terminal 205-1 shown in FIG. 21 receives a notification using an e-mail from the management server 105, the communication terminal 205-1 displays the notification using an e-mail application. In the example shown in FIG. 27, the communication terminal 205-1 displays a notification of "It seems you are feeling ill recently. Why don't you take a medical checkup?" using an e-mail application.

In this way, in this embodiment, the management server 105 compares the operation method of the communication terminal 205-1 performed by the target person with the operation method registered in advance in the database 125, and when the operation method of the terminal 205-1 is determined to be outside the range previously registered in the database 125, the management server 105 issues a notification to the communication terminal 205-1 or the communication terminal 205-2. Therefore, the target person who possesses the communication terminal 205-1 or the family who possesses the communication terminal 205-2 can obtain correct information about the condition of the target person who possesses the communication terminal 205-1. Further, when the operation method of the communication terminal 205-1 performed by the target person is within the range registered in advance in the database 125, the management server 105 does not issue a notification. By doing so, it is possible to prevent an increase in communication traffic caused by unnecessary notifications.

Modified Example

In the above-described forms, in order to detect an abnormality in the condition of the target person, a determination is made about whether an answer to a question is correct and about an operation method such as how to answer and hang up a call based on a tone of the target person's speech. Alternatively, a determination may be made based on a detection of another sound such as coughing, sneezing, sigh, etc., other than usual speaking voices, whether the target person is speaking smoothly, whether the target person is at a loss for a word, whether the target person stumbles, and an amount of speech, which are to be used in the comparison. Further, in the fifth and sixth embodiments, the comparison for the time from a question to an answer has been described. Likewise, a detection may be made about the target person not being able to put into words. Similarly, a detection may be made about a content input (spoken) by the target person being completely different from a content registered in the database. Furthermore, a detection may be made about an erroneous operation by an operator such as an operation on a button which should not be operated among operation buttons of the communication terminal.

Although descriptions are made above by assigning each function (process) to each component, this assignment is not limited to the above. Moreover, the above-described forms of the configuration of the components are merely an example and not limited to this.

The processing performed by each component provided in each of the notification systems 100, 102, and 104 and the management servers 101, 103, and 105 described above may be performed by a logic circuit prepared according to each purpose. Further, a computer program (hereinafter referred to as a program) in which processing contents are described as a procedure may be recorded on a recording medium that can be read by each of the notification systems 100, 102, and 104 and the management servers 101, 103, and 105, and the program recorded on this recording medium may be read into and executed by each of the notification systems 100, 102, and 104 and the management servers 101, 103, and 105. The recording medium that can be read by each of the notification systems 100, 102, and 104 and the management servers 101, 103, and 105 indicates a transferable recording medium such as a floppy (registered trademark) disk, a magneto-optical disk, a DVD (Digital Versatile Disc), a CD (Compact Disc), and Blu-ray (registered trademark) Disc, and memories such as a ROM (Read Only Memory) and RAM (Random Access Memory) and a HDD (Hard Disc Drive) built into each of the notification systems 100, 102, and 104 and management servers 101, 103, and 105. The program recorded on this recording medium is read by a CPU provided in each of the notification systems 100, 102, and 104 and the management servers 101, 103, and 105, and the same processing as described above is performed under the control of the CPU. Here, the CPU operates as a computer that executes a program read from the recording medium on which the program is recorded.

The whole or part of the above embodiments can be described as, but not limited to, the following supplementary notes.

(Supplementary Note 1)

A notification system comprising:

calling means for making a call to a communication terminal possessed by a target person;

a database configured to store in advance speech data of the target person;

comparison means for comparing a tone of speech data transmitted from the communication terminal with a tone of the speech data stored in the database; and notification means for issuing a predetermined notification when a difference between the tone of the speech data transmitted from the communication terminal and the tone of the speech data stored in the database is determined to be outside a predetermined range as a result of the comparison by the comparison means.

(Supplementary Note 2)

The notification system according to Supplementary note 1, wherein the notification means issues the notification to a communication terminal associated in advance with the communication terminal possessed by the target person.

(Supplementary Note 3)

The notification system according to Supplementary note 1 or 2, wherein the notification means issues the notification to the communication terminal possessed by the target person.

(Supplementary Note 4)

The notification system according to any one of Supplementary notes 1 to 3, wherein the calling means transmits a message prompting the target person to speak to the communication terminal possessed by the target person.

(Supplementary Note 5)

The notification system according to Supplementary note 4, wherein the calling means transmits a question associated in advance with the target person as the message.

(Supplementary Note 6)

The notification system according to any one of Supplementary notes 1 to 5, wherein the comparison means makes the comparison based on at least one of a voice pitch, a speaking speed, an intonation, and an accent as the tone of the speech data.

(Supplementary Note 7)

The notification system according to any one of Supplementary notes 1 to 6, wherein the notification means issues the notification using an e-mail.

(Supplementary Note 8)

The notification system according to any one of Supplementary notes 1 to 6, wherein the notification means issues the notification using an SMS (Short Message Service).

(Supplementary Note 9)

The notification system according to any one of Supplementary notes 1 to 6, wherein the notification means issues the notification using a voice call.

(Supplementary Note 10)

The notification system according to any one of Supplementary notes 1 to 9, further comprising update means for updating the speech data stored in the database based on the speech data in a call to the communication terminal possessed by the target person.

(Supplementary Note 11)

A notification method comprising:

a process of making a call to a communication terminal possessed by a target person;

a process of comparing a tone of speech data transmitted from the communication terminal with a tone of the speech data stored in a database which stores speech data of the target person in advance; and a process of issuing a predetermined notification when a difference between the tone of the speech data transmitted from the communication terminal and the tone of the speech data stored in the database is determined to be outside a predetermined range as a result of the comparison.

(Supplementary Note 12)

A non-transitory computer readable medium storing a program that causes a computer to execute:

a procedure of making a call to a communication terminal possessed by a target person;

a procedure of comparing a tone of speech data transmitted from the communication terminal with a tone of the speech data stored in a database which stores speech data of the target person in advance; and a procedure of issuing a predetermined notification when a difference between the tone of the speech data transmitted from the communication terminal and the tone of the speech data stored in the database is determined to be outside a predetermined range as a result of the comparison.

This application claims priority to Japanese Patent Application No. 2017-117008, filed on Jun. 14, 2017, the entire disclosure of which is incorporated herein.

REFERENCE SIGNS LIST 100, 102, 104 NOTIFICATION SYSTEM
101, 103, 105 MANAGEMENT SERVER
110, 111, 112, 113, 114, 115 CALLING MEANS
120, 121, 122, 123, 124, 125 DATABASE
130, 131, 132, 133, 134, 135 COMPARISON MEANS
140, 141, 142, 143, 144, 145 NOTIFICATION MEANS
151 UPDATE MEANS
200, 201-1, 201-2, 202, 203-1, 203-2, 204, 205-1, 205-2 COMMUNICATION TERMINAL
301, 303, 305 COMMUNICATION NETWORK

The invention claimed is:

1. A notification system comprising:
at least one memory configured to store one or more instructions; and
at least one processor configured to execute the one or more instructions to:
make a call to a communication terminal possessed by a target person;
store in advance speech data of the target person in a database;
compare a tone of speech data transmitted from the communication terminal with a tone of the speech data stored in the database;
issue a predetermined notification when a difference between the tone of the speech data transmitted from the communication terminal and the tone of the speech data stored in the database is determined to be outside a predetermined range as a result of the comparison; and
learn the speech data in a call to the communication terminal possessed by the target person and update the speech data stored in the database by reflecting the learned result in the database.

2. The notification system according to claim 1, wherein the processor is further configured to issue the notification to a communication terminal associated in advance with the communication terminal possessed by the target person.

3. The notification system according to claim 1, wherein the processor is further configured to issue the notification to the communication terminal possessed by the target person.

4. The notification system according to claim 1, wherein the processor is further configured to transmit a message prompting the target person to speak to the communication terminal possessed by the target person.

5. The notification system according to claim 4, wherein the processor is further configured to transmit a question associated in advance with the target person as the message.

6. The notification system according to claim 1, wherein the processor is further configured to make the comparison based on at least one of a voice pitch, a speaking speed, an intonation, and an accent as the tone of the speech data.

7. The notification system according to claim 1, wherein the processor is further configured to issue the notification using an e-mail.

8. The notification system according to claim 1, wherein the processor is further configured to issue the notification using an SMS (Short Message Service).

9. The notification system according to claim 1, wherein the processor is further configured to issue the notification using a voice call.

10. A notification method comprising:
- making a call to a communication terminal possessed by a target person;
- comparing a tone of speech data transmitted from the communication terminal with a tone of the speech data stored in a database which stores speech data of the target person in advance;
- issuing a predetermined notification when a difference between the tone of the speech data transmitted from the communication terminal and the tone of the speech data stored in the database is determined to be outside a predetermined range as a result of the comparison; and
- learning the speech data in a call to the communication terminal possessed by the target person and updating the speech data stored in the database by reflecting the learned result in the database.

11. A non-transitory computer readable medium storing a program, when executed by a processor, causes a computer to:
- make a call to a communication terminal possessed by a target person;
- compare a tone of speech data transmitted from the communication terminal with a tone of the speech data stored in a database which stores speech data of the target person in advance;
- issue a predetermined notification when a difference between the tone of the speech data transmitted from the communication terminal and the tone of the speech data stored in the database is determined to be outside a predetermined range as a result of the comparison; and
- learn the speech data in a call to the communication terminal possessed by the target person and updating the speech data stored in the database by reflecting the learned result in the database.

* * * * *